United States Patent [19]
Lowell

[11] Patent Number: 5,985,284
[45] Date of Patent: Nov. 16, 1999

[54] ORAL OR INTRANASAL VACCINES USING HYDROPHOBIC COMPLEXES HAVING PROTEOSOMES AND LIPOPOLYSACCHARIDES

[76] Inventor: George H. Lowell, 6303 Western Run Dr., Baltimore, Md. 21215

[21] Appl. No.: 08/677,302

[22] Filed: Jul. 9, 1996

Related U.S. Application Data

[63] Continuation of application No. 08/673,756, Apr. 29, 1996, which is a continuation of application No. PCT/US93/10402, Oct. 29, 1993.

[51] Int. Cl.[6] .................................................. A61K 39/02
[52] U.S. Cl. ...................... 424/234.1; 424/249.1; 424/250.1; 424/203.1; 424/197.11; 424/193.1; 536/123.1
[58] Field of Search ............................. 424/234.1, 249.1, 424/250.1, 203.1, 193.1, 197.11; 536/123.1

[56] References Cited

U.S. PATENT DOCUMENTS 4,707,543  11/1987  Zollinger et al. ..................... 530/402

OTHER PUBLICATIONS

Black et al. 1987. J. Infect. Dis. 155(6): 1260–1264.
Lowell et al. 1988. Science, 240: 800–802.
Cohen et al. 1988. J. Infect. Dis. 157(5): 1068–1071.
Lowell et al. 1988. J. Exp. Med. 167: 658–663.
Ruegg et al. 1990. J. Immunol. Methods. 135: 101–109.
Orr et al. American Society for Microbiol. 93rd Gen. Meeting. May 16–20, 1993. Atlanta. E–58 & E59.
Orr et al. Nov. 1994. Infect. Immun. 62(11): 5198–5200.
Mallett et al. Jun. 1995 Infect. Immun. 63(6): 2382–2386.
Orr et al. Jun 1993. Infect. Immun. 61(6): 2390–2395.
Livingston et al. 1993. Vaccine. 11(12): 1149–1203.

*Primary Examiner*—James C. Housel
*Assistant Examiner*—Jennifer Graser
*Attorney, Agent, or Firm*—Morrison & Foerster LLP

[57] ABSTRACT

An immunogenic complex, essentially consisting of neisserial outer membrane protein proteosomes hydrophobically complexed to native purified bacterial lipopolysaccharide and formulated in accordance with the current invention for mucosal delivery such as via the oral or intranasal route is used as a vaccine. Specifically, a vaccine using shigella lipopolysaccharides complexed to proteosomes for such mucosal administration induces IgG and IgA antibodies in sera and in respiratory and intestinal fluids. Furthermore, such antibodies are associated with protection against shigella infection and these vaccines are herein demonstrated to protect against mucosal infection with shigella.

16 Claims, 9 Drawing Sheets

☒ 50 μg SEB-Toxiod F + Proteosomes

FIG. 3

Protein and LPS levels in fractions eluted from a CL-4B column after application of the prot-S. flexneri 2a LPS complex and LPS levels in column fractions after application of S. flexneri 2a LPS alone.

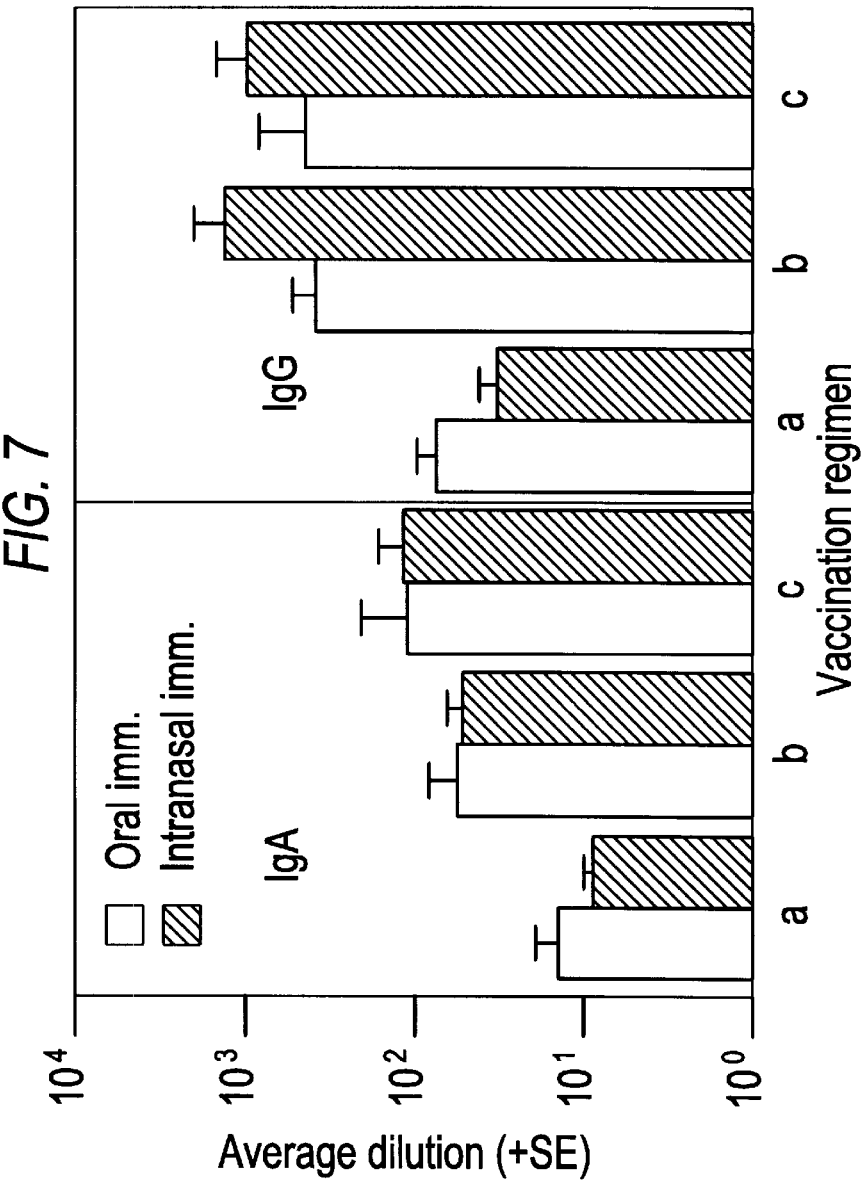

FIG. 7

Anti-LPS IgG and IgA in sera of mice immunized either orally or intranasally with prot-LPS complex. Four or five animals were immunized either with two doses at 0 and 1 weeks (a), with two doses at 0 and 3 weeks (b), or with three doses at 0, 1, and 4 weeks (c). The results are expressed as the geometric mean of the maximal dilution elicited an optical density greater than 0.5 after 1 h of incubation with substrate.

Anti-LPS IgA in intestines and lungs of mice immunized either orally or intranasally with prot-LPS complex as described in the legend to Fig. 3. The results are expressed as the geometric mean of the maximal dilution elicited an optical density greater than 0.5 (intestines) or 0.2 (lungs) after 2 h of incubation with substrate.

Inhibition of specific antibody binding to solid-phase S flexneri 2a LPS in ELISA. LPSad, prot-LPSad, LPS, or prot-LPS was incubated with LPS-positive guinea pig serum prior to its application to an ELISA.

ORAL OR INTRANASAL VACCINES USING HYDROPHOBIC COMPLEXES HAVING PROTEOSOMES AND LIPOPOLYSACCHARIDES

CROSS-REFERENCES TO RELATED APPLICATIONS

This application is a continuation of application Ser. No. 08/673,756 filed Apr. 29, 1996 which is a continuation of PCT US 93/10402 filed Oct. 29, 1993.

GOVERNMENT INTEREST

The invention described and claimed herein may be manufactured, licensed and used by or for governmental purposes without the payment of any royalties thereon.

BACKGROUND OF THE INVENTION

1. FIELD OF THE INVENTION

This invention relates to the use of oil-in-water submicron emulsions as vaccine adjuvants for enhancing the immunogenicity and improvement of the immune response of antigens and to methods and compositions for preparing them. The invention further relates to a novel vaccine delivery system using proteosomes hydrophobically completed to lipopolysaccharides and formulated for oral or intranasal administration to induce protective antibodies in sera and/or respiratory and/or intestinal secretions that are associated with protection against disease.

2. BACKGROUND OF THE INVENTION

In the past, the risks of whole-pathogen vaccines and limited supplies of useful antigens posed barriers to development of practical vaccines. Today, the tremendous advances of genetic engineering and the ability to obtain many synthetic recombinant protein antigens derived from parasites, viruses, and bacteria has revolutionized the development of new generation vaccines.

Although the new, small synthetic antigens offer advantages in the selection of antigenic epitopes and safety, a general drawback of small antigens is poor immunogenicity, resulting in low antibody titers and the need for repeated immunizations. This lack of immunogenicity has created an acute need to identify pharmaceutically acceptable delivery systems or adjuvants for these new antigens.

To improve the immune response antigens are usually mixed with adjuvant substances that stimulate immunogenicity. Immunological adjuvants have generally been divided into two basic types: aluminum salts and oil emulsions.

Aluminum phosphate and hydroxide (alum) have a long history of use as adjuvants. They are the only ones recognized as safe for this use by the Food and Drug Administration. Antibody levels against antigens in alum-based vaccines are clearly, although moderately, elevated above those obtained with the corresponding aqueous vaccine. However, aluminum compounds have not always enhanced the immunogenicity of vaccines, and the problem of inconsistent antibody production has been frequently cited. Occasional production of sterile abscesses and persistent nodules were also reported with alum-adjuvanted vaccines. Regarding long term side effects, researchers have suggested a link between aluminum and diseases of the brain, including Alzheimer's disease (Edelman, R.: Vaccine adjuvants. Rev. Inf. Dis. 1980; 2:370–383).

The development of emulsified oil adjuvants emerged historically from the studies of J. Freund who observed a remarkable increase in both the antibody and delayed hypersensitivity response to killed mycobacteria if the organisms were incorporated in paraffin oil. There are two types of Freund's mineral-oil adjuvants: Incomplete Freund's Adjuvant (IFA), consisting of an approximately 50:50 water-in-oil emulsion, and complete Freund's adjuvant (CFA), a similar preparation with inclusion of killed mycobacteria. The powerful antibody-stimulating effect of CFA has not been surpassed by any other adjuvant. However, because of severe pain, abscess formation, fever and granulomatous inflammation, CFA can be used only for experimental purposes and not in human or veterinary vaccines. The toxic reactions reported using mineral oil-adjuvanted vaccines were attributed to impurities in Arlacel A (principally mannide monooleate), the emulsifying agent used in the preparations.

The use of IFA in humans has been limited to those clinical situations in which aqueous vaccines are relatively impotent and aluminum compounds have not provided enough adjuvant activity. J. Salk made practical the use of IFA in human vaccines by using a highly refined mineral oil and a purified Arlacel A emulsifier free of toxic substances injected intramuscularly in thousands of recipients. However, occasional failure of IFA vaccines reported in humans, and the discovery that Arlacel A was carcinogenic in mice, despite the absence of increased tumor formation in humans, has restricted the use of IFA vaccine formulations.

Since CFA was the first successful adjuvant, most investigators followed the example of CFA in assuming that substitutes for each of the three components, viz. oil, emulsifier and immunostimulant, are necessary for formulating a successful adjuvant.

U.S. Pat. Nos. 4,772,466 and 4,606,918 disclose methods for enhancing the immunogencity of an antigen by emulsifying it with a polyoxypropylenepolyoxyethylene block polymer, a glycol ether-based surfactant, a metabolizable non-toxic oil, and an immunopotentiating amount of an immunostimulating glycopeptide.

Pharmaceutical compositions comprising an oil-in-water micron size emulsion, refined detoxified endotoxin, cell wall skeleton and trehalose dimycolate have been disclosed as vaccine adjuvants (U.S. Pat. Nos. 4,505,900 and 4,803,070).

International patent application (PCT) WO 90/14837 discloses adjuvant composition comprising a metabolizable oil and emulsifying agent in the form of an oil-in-water emulsion, where the antigen is added externally to the prepared emulsion (extrinsic formulation). All the examples in the disclosure contained the immunostimulating agent, MTP-PE, a lipophilic muramyl peptide derivative.

*Shigella flexneri* and other Shigella species present another unique challenge as a disease vector. Shigella represent a major cause of diarrheal diseases in developing countries (Keusch, G. T. and M. L. Bennish. 1991. in Evans A S and Brachman P S ed. Bacterial Infection of Human 2$^{nd}$ ed. New York and London: Plenum Medical p. 593.). It has been shown that type specific protection against shigellosis can be acquired in man after infection with a wild type or attenuated bacteria (Cohen, D. et al. 1988. J. Infec. Dis. 157:1068.; Herrington, D. A. et al. 1990. *Vaccine.* 8:353; Black, R. E. et al. 1987. J. Infect. Dis. 155:1260.) and there is direct evidence that anti-type-specific LPS antibodies are associated with this protection (Cohen, D. et al. 1988. J. Infec. Dis. 157:1068.; Black, R. E. et al. 1987. J. Infect. Dis. 155:1260). It is widely agreed that local mucosal immune responses, especially secretory immunoglobulins including IgA and IgG play a major role in protection against such mucosal enteric pathogens following mucosal immunization or natural exposure; serum levels of these antibodies may be a measure or marker reflecting the production of local antibodies and, as such, may also indicate or contribute to protection (Underdown, B. J. and J. M. Schiff. 1986. Ann. Rev. Immunol. 4: 389–417; Cohen, D. et al. 1988. J. Infec. Dis. 157:1068.).

Since the demonstration in 1967 (Formal, S. B. et al. 1967. Proc. Soc. Exp. Biol. Med. 25: 347–349) that parenteral immunization with live or killed shigella bacteria was ineffective in protecting against oral challenge or monkeys with shigella, the major thrust of research has focused on the use of live attenuated or genetically constructed vaccines (Formal, S. B. and M. M. Levine. in Bacterial Vaccines, pp. 167–186). The problems associated with development of successful live vaccines include the narrow window between efficacy and safety of such vaccines since their ability to cause disease and side effects can be exceedingly dose dependant. The novelty of the current approach is emphasized by the fact that results of immunogenicity and protection in established animal models of disease were achieved despite using a sub-unit, non-living vaccine delivery system that is safe for intranasal or oral delivery. While several other approaches to the problem of development of oral or intranasal vaccines to protect against mucosal diseases in the gastro-intestinal or respiratory tract have been explored, none uses the technology of the instant invention; nor have they been effective in demonstrating induction of high levels of IgA and IgG in both mucosal secretions and sera as well as protection in established animal models as is here shown.

Proteosomes have previously been used with peptides (U.S. patent application Ser. No. 07/642,093 filed Jan. 16, 1991 which is a Continuation of Ser. No. 07/065,440 filed Jun. 23, 1987) and large proteins (U.S. patent application entitled "Immunopotentiating System for Large Proteins and Polypeptides" Ser. No. 07/336,952, filed Apr. 12, 1989) in vaccine development of parenteral vaccines and Zollinger et al. (U.S. Pat. No. 4,707,543; Nov. 17, 1987) have used meningococcal outer membrane proteins non-covalently complexed to detoxified lipopolysaccharides or polysaccharides in parenteral vaccines. The Zollinger work, however, specifically teaches away from the instant invention since the thrust of their work emphasizes that detoxified LPS or polysaccharide can be used whereas in the instant invention, detoxified LPS, in direct contrast to the non-detoxified LPS, is entirely ineffective. Furthermore, Zollinger neither showed, claimed nor suggested that his vaccines would be effective when delivered via the oral or intranasal route.

3. SUMMARY OF THE INVENTION

The present invention provides emulsions comprising a plurality of submicron oil-in-water droplets of a particle size in the range of 50 nm to 500 nm that effect enhanced immunogenicity of antigens incorporated intrinsically or extrinsically into the particles. Therefore the submicron emulsion (SME) particles of the present invention can be used as vaccine adjuvants.

In marked contrast to the aforementioned disclosures, as will be described, the present invention does not require use of any immunostimulatory mycobacteria or muramyl peptide-like additives for its submicron emulsion to be effective. Moreover, as will be seen, a preferred embodiment of the present invention consists of intrinsically incorporating the antigen into the emulsion at the time of formation of the emulsion; this is in distinct contrast to mixing the antigen with the emulsion after the emulsion has been independently extrinsically formed. It will be appreciated that intrinsic formulation will be effective even in situations and conditions and species where extrinsic formulation is not. In this regard as well, the present invention is uniquely different and not at all implied by the previously mentioned applications which indeed teaches away from the present invention in stating that it is sufficient to simply mix the antigen with the extrinsically previously formed emulsion.

The vaccine formulations of this invention also do not include any polyoxypropylene-polyoxyethylene block polymer, trehalose dimycolate, or cell wall skeleton, as are found in prior art compositions.

Another aspect of this invention is to provide compositions and methods for the preparation of submicron emulsions containing antigens, incorporated either intrinsically (emulsified together with the oil and surfactant) or extrinsically (added externally to prepared SME).

In some cases, the submicron emulsion of the present invention can be administered in combination with other vaccine delivery systems, such as proteosomes, as indicated in the examples.

The size, concentration and specific formulation of SMEs may be varied to suit the particular antigen used. Moreover, such adjuvant preparations may enhance both humoral and cell-mediated immunity (CMI) as do Freund's adjuvants. The SMEs here described have been developed for human use and since the oily droplets of the emulsions are of submicron size and contain no added pyrogenic moieties such as mycobacteria or MDP derivatives they have, unlike Freund's adjuvants, great safety potential. They may be especially applicable to antigens that are vaccine candidates to protect against biologic toxins or infectious agents which have natural hydrophobic moieties as a component including transmembrane viral, bacterial or parasite proteins, membrane proteins such as proteosomes, lipopolysaccharides, glycolipids such as gangliosides, or a variety of proteins or peptides to which hydrophobic anchors have been chemically or genetically added.

Another aspect of the invention provides compositions and methods to achieve mucosal immunity by using an emulsion comprising a plurality of submicron particles, a mucoadhesive macromolecule, immunogenic peptide or antigen, and an aqueous continuous phase, which induces mucosal immunity by achieving mucoadhesion of the emulsion particles to mucosal surfaces. Mucous surfaces suitable for application of the emulsions of the present invention may include ocular (corneal, conjunctival), oral (buccal, sublingual), nasal, vaginal and rectal routes of administration.

The emulsion particles have a hydrophobic core comprising a lipid or lipid-like composition and are stabilized with amphiphilic and/or non-ionic surfactants.

A wide variety of immunogens, including both water-soluble and water-insoluble peptides or polysaccharides, may be accommodated in the present emulsions. The hydrophobic core and surfactant provide a microenvironment which accommodates lipophilic immunogens such as lipid A or lipopolysaccharides as well as membrane-associated peptide antigen domains, while the aqueous continuous phase accommodates water-soluble peptide domains, or oligosaccharides.

The term "peptide" herein includes both oligopeptides and proteins. To facilitate intestinal uptake, the emulsions may be encapsulated in gelatin capsules or otherwise enterocoated to prevent their exposure to gastric fluids when the oral route of administration is selected. Furthermore, the emulsions may be lyophilized as disclosed previously (Pharmos, PCT/US 93 01415) prior to their encapsulation in order to achieve added stability of the antigen.

Another invention is a desirable vaccine using lipopolysaccharide (LPS), e.g. *Shigella flexneri* 2a, *Shigella sonnei* or other shigella lipopolysaccharide (LPS), complexed with proteosomes to induce anti-LPS antibodies in the aforementioned fluids in the absence of SME particles which protects against homologous shigella infection in a well-known animal model of shigellosis. The data disclosed herein shows that the instant invention can be used as an oral or intranasal non-living sub-unit vaccine to protect against mucosal diseases of the gastro-intestinal tract such as shigellosis. In addition, since high antibody levels are induced in either the respiratory or gastro-intestinal tracts following either oral or intranasal immunization, and since protection is shown against either conjunctival or respiratory challenge, these proteosome-based vaccines and there associated methodologies can also be used to protect against diseases that enter the body via respiratory, ocular or gastro-intestinal routes. These vaccines should also result in protection against mucosal diseases of the urogenital and auditory tracts.

4. BRIEF DESCRIPTION OF THE FIGURES

FIG. 3 shows the immunogenicity of SEB-Toxoid F complexed to proteosomes as a free antigen or adjuvanted with alum or extrinsic SME.

FIG. 7 is a graph depicting Serum IgG and IgA in mice as determined by ELISA. Mice were immunized either orally or intranasally with prot-LPS complex using *S. flexneri* 2a LPS or *S. Sonnei* LPS. The results are expressed as the maximal reciprocal dilution which gave an O.D. greater than 0.5 after 1 hr (IgG) or 0.2 after 2 hrs (IgA) processing with substrate.

Figure 8:
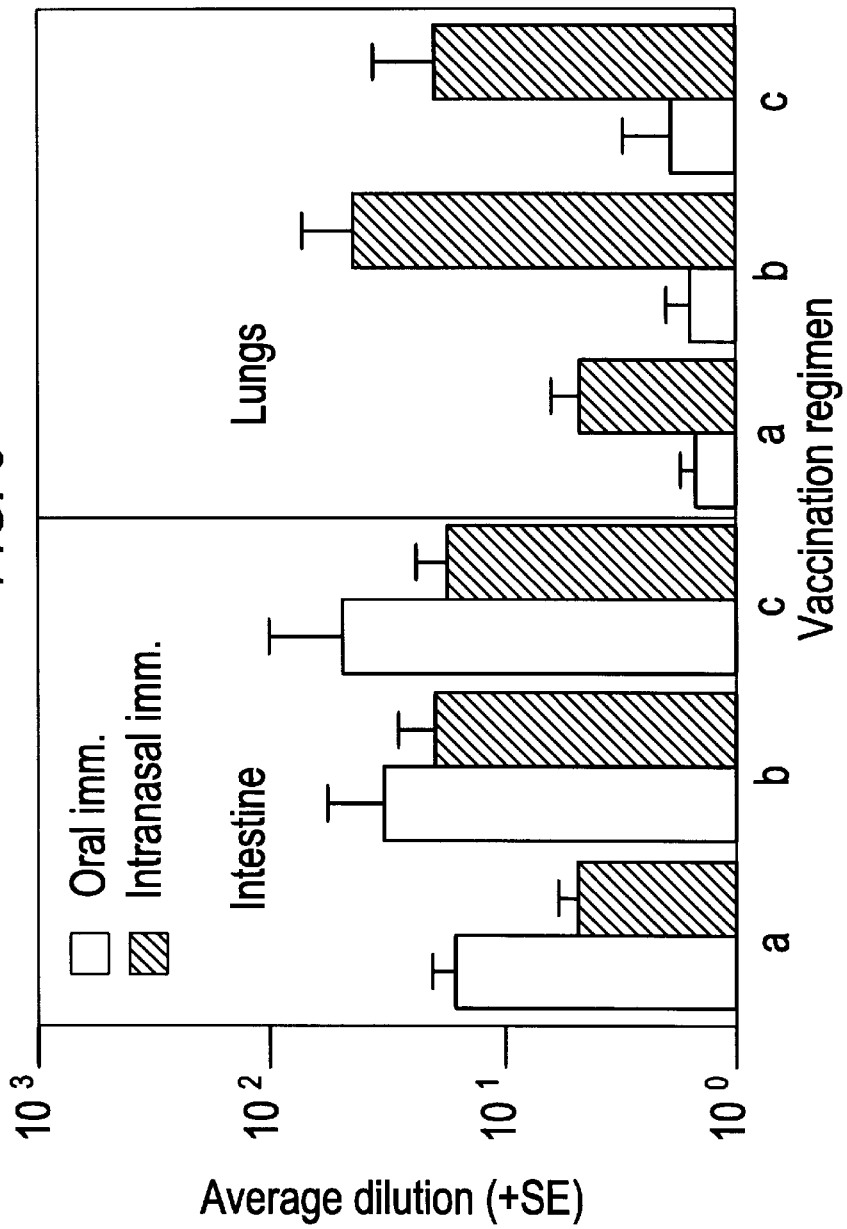

FIG. 8 provides Intestinal and lung IgA in mice as determined by ELISA. Mice were immunized either orally or intranasally with prot-LPS complex using *S. flexneri* 2a LPS or *S. Sonnei* LPS. The results are expressed as the maximal reciprocal dilution which gave an O.D. greater than 0.5 (intestine) or 0.2 (lungs) after 2 hrs processing with substrate.

Figure 9:
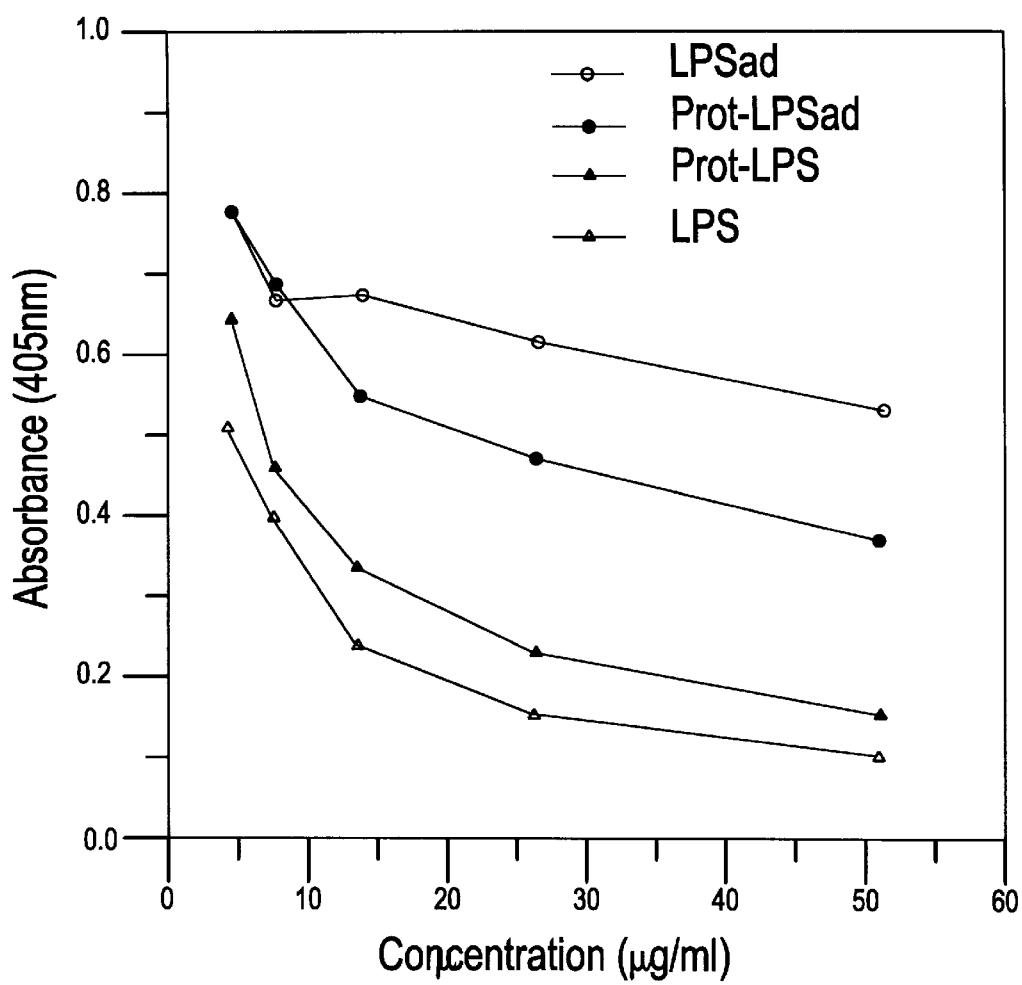

FIG. 9 shows inhibition of specific antibody binding to solid-phase *S. flexneri* 2a LPS in ELISA. LPSad, prot-LPSad, LPS, or prot-LPS was incubated with LPS-positive guinea pig serum prior to its application to an ELISA.

5. DETAILED DESCRIPTION OF THE INVENTION

This invention is directed to pharmaceutical compositions comprising submicron emulsions as vaccine adjuvants, and to methods for preparing and using such compositions.

5.1 Features of the Submicron Emulsion (SME) Particles

The submicron emulsion vaccine adjuvants of the present invention comprise an aqueous continuous phase suspending a colloidal phase of submicron particles. The particles have a weighted average diameter of 50 to 500 nm, more preferably 70 to 300 nm. In many embodiments, the weighted average diameter be less than 460 nm, 400 nm, 300 nm, or 200 nm.

Usually the diameter will be greater than 40 nm or 50 nm, and frequently is greater than 70 nm. Often, the above-stated upper and lower diameter ranges will include both the weighted average and at least one standard deviation of particle diameter.

The emulsion particle comprises a hydrophobic core, often including or even consisting essentially of a metabolizable and non-toxic oil such as MCT (medium chain triglycerides) oil of the type extensively used in parenteral emulsions like Intralipid® or a vegetable oil.

Optionally, other hydrophobic lipids may be used, including cholesterol or cholesteryl esters and fatty acids. In many embodiments, the core of the particles will be substantially free of protein other than the antigen to be delivered, i.e. less than 1% (w/w), and in most cases less than 0.1% of other protein.

The emulsion usually further comprises at least one surfactant, which may be a natural biologically compatible surfactant such as phospholipid (e.g., lecithin) or a pharmaceutically acceptable non-natural surfactant such as Tween-80. The surfactant assists in maintaining particles within the desired size range and preventing their aggregation.

In many embodiments the emulsion may be formed and stabilized in the substantial absence of one or more cosurfactants selected from the group, consisting of an unhalogenated aliphatic C3–C6 alcohol, a free fatty acid, a mono- or di-glyceride, a polyglycerol fatty acid ester, or a lysophosphatidyl choline. One or all of the above-named cosurfactants may comprise less than 5%, commonly less than 1%, and frequently less than 0.1% (w/w) relative to the weight of the hydrophobic core.

The emulsion also contains an immunogen. The antigen may be hydrophilic, hydrophobic, or amphiphilic since the emulsion provides a biphasic lipophilic-hydrophilic microenvironment.

The continuous phase of the emulsion is aqueous, and may contain salts, sugars, antioxidants, preservatives, microbicides, buffers, osmoticants, cryoprotectants, and other pharmaceutically useful additives or solutes.

Bioadhesive polymers, such as those currently used in pharmaceutical preparations optionally may be added to the emulsion to further enhance the immunogenicity through mucous membranes achieving mucosal immunity.

The concentrations indicated by % in the following description denote the concentration by weight of the component per 100 units volume of the entire composition.

All indicated concentrations should be understood as standing each by itself, and not cumulative. It should be appreciated by the artisan, however, that there is some dependency between the concentrations of the components, e.g. higher concentrations of the oil will generally require higher concentrations of the emulsifier and surfactant.

The emulsion used in the vaccine compositions of the present invention may comprise about 0.5 to 50% oil, about 0.1 to 10% emulsifier and about 0.05 to 5% of the non-aqueous phase, i.e. the combined concentration of the oily and the amphiphilic phase, increases viscosity of the composition. In order to obtain a non-viscous composition, the concentration of the non-aqueous phase should generally not exceed about 25%.

Preferred concentrations of the components are as follows: about 1 to 20% oil, most preferably about 1 to 10% for a composition intended to be fluid, about 0.2 to 5% of the emulsifier, with about 0.2 to 5% for the surfactant, with about 0.2 to 1% being particularly preferred.

The antigen is present in an amount of about 0.001 to 5% by weight of the composition, preferably about 0.1 to 2.5%. Depending upon whether the antigen is hydrophilic or hydrophobic, it will be physically present in the oily phase at the oil-water interface, or the aqueous component. Also, the pH of these compositions should be in a range which is suitable for the stability of the antigen.

The submicron emulsion adjuvant formulations of this invention differ from the emulsion adjuvant composition of patent application WO 90/14837 in the following features:

(i) all the compositions described in the above mentioned application are prepared extrinsically, namely the antigens are added externally to the previously prepared emulsion by mixing, while in the present invention the antigen can be added either extrinsically or more preferably intrinsically, together with all the emulsion components before emulsification and prior to the mixture of oil and water phases as detailed in the examples;

(ii) all the examples in the above mentioned disclosure contain an immunopotentiating amount of an immunostimulating glycopeptide of the type of muramyl peptides or their lipophilic derivatives, such as MTP-PE, while in the present invention all the SME adjuvant compositions are prepared in the absence of any muramyl peptide immunostimulating agent.

5.2 Composition of the Hydrophobic Core

A hydrophobic compound which is suitably non-toxic may be used as a component of the core. Examples include triglycerides, preferably of food grade purity or better, which may be produced by synthesis or by isolation from natural sources. Natural sources may include animal fat or vegetable oil, e.g., soya oil, a source of long chain triglycerides (LCT). Other triglycerides of interest are composed predominantly of medium length fatty acids, denoted medium chain triglycerides (MCT). A medium chain triglyceride (MCT) oil, is a triglyceride in which the carbohydrate chain has 8–12 carbons. Although MCT oil can be considered as a component of vegetable oil, it is separately identified herein because of its particular utility as a preferred oil for use in the present emulsions. In addition, MCT oil is available commercially. Examples of such MCT oils include TCR (trade name of Societe Industrielle des Oleagineuax, France, for a mixture of triglycerides wherein about 95% of the fatty acid chains have 8 or 10 carbons) and MIGLYOL 812 (trade name of Dynamit Nobel, Sweden for a mixed triester of glycerine and of caprylic and capric acids). The fatty acid moieties of such triglycerides may be unsaturated, monounsaturated or polyunsaturated; mixtures of triglycerides having various fatty acid moieties are acceptable. The core may comprise a single hydrophobic compound or a mixture of compounds.

Examples of vegetable oils include soybean oil, cotton seed oil, olive oil, sesame oil and castor oil. Oily fatty acids, such as oleic acid and linoleic acid, fatty alcohols, such as oleyl alcohol, and fatty esters, such as sorbitan monooleate and sucrose mono-, di- or tripalmitate, can be used as the oil component, although these are not as preferred as the other oils mentioned above.

Optionally, the core may contain cholesterol or cholesteryl esters. In many embodiments, cholesteryl esters or cholesterol comprise less than 10%, 5%, 1%, or even 0.1% (w/w) of the total hydrophobic components of the core.

Considerations in choice of core material include low toxicity and irritancy, biocompatibility, safety, metabolizability, stability and high loading capacity for antigens. Preferred hydrophobic core components have molecular weights below about 5,000 Da, more preferably below about 2,000 Da, and most preferably below about 1,500 Da.

5.3 Composition of Surfactant Component

The amphiphilic phase comprises the emulsifiers and surfactants. Preferred emulsifiers include a phospholipid compound or a mixture of phospholipids. Suitable components include lecithin; EPICURON 120 (Lucas Meyer, Germany) which is a mixture of about 70% of phosphatidylcholine, 12% phosphatidylethanol-amine and about 15% other phospholipids; OVOTHIN 160 (Lucas Meyer, Germany) which is a mixture comprising about 60% phosphatidylcholine, 18% phosphatidylethanol-amine and 12% other phospholipids; a purified phospholipid mixture; LIPOID E-75 or LIPOID E-80 (Lipoid, Germany) which is a phospholipid mixture comprising about 80% phosphatidyl-choline, 8% phosphatidylethanol-amine, 3.6% non-polar lipids and about 2% sphingomyelin. Purified egg yolk phospholipids, soybean oil phospholipids or other purified phospholipid mixtures are useful as this component. This listing is representative and not limiting, as other phospholipid materials which are known to those skilled in the art can be used.

Some embodiments of the invention provide an improved bioadhesive emulsion comprising incorporation of an amphiphilic and/or nonionic surfactant such as phosphatidylcholine, Tween, etc., together with a mucoadhesive polymer macromolecule as described in Section 5.6.

Particularly suitable emulsifiers include phospholipids, which are highly biocompatible. Especially preferable phospholipids are phosphatidyl-cholines (lecithins), such as soy or egg lecithin. Other suitable phospholipids include phosphatidylglycerol, phosphatidylinositol, phosphatidylserine, phosphatidic acid, cardiolipin, and phosphatidyl-ethanolamine. The phospholipids may be isolated from natural sources or prepared by synthesis. Phospholipid surfactants are believed usually to form a single monolayer coating of the hydrophobic core.

The surfactant is believed in many embodiments to interact with the bioadhesive polymer to form a hydrated polymer film coating associated with the surfactant at the stabilized lipid/water interface surrounding the particle core.

Preferred compositions contain a surfactant component. The surfactant stabilizes the outer surface of the hydrophobic core component of the emulsion particles, thereby promoting a more uniform and manipulatable particle size. Usually the surfactant is present in a proportion of 0.01% to 5% (w/w) of the emulsion, preferably 0.05% to 2%.

Typically, the weight percentage of surfactant relative to hydrophobic (oil or other lipid) component is from 0.2% to 50%, more preferably from 5% to 20%. Higher ratios of surfactant to core lipid tend to promote smaller particle core diameters.

Surfactants may be either natural compounds, such as phospholipids and cholates, or non-natural compounds such as: polysorbates, which are fatty acid esters of polyethoxylated sorbitol (Tween); polyethylene glycol esters of fatty acids from sources such as castor oil (Emulfor); polyethoxylated fatty acid, e.g. stearic acid (Simulsol M-53); Nonidet; polyethoxylated isooctylphenol/formaldehyde polymer (Tyloxapol); polyoxyethylene fatty alcohol ethers (Brij); polyoxyethylene nonphenyl ethers (Triton N); polyoxyethylene isooctylphenyl ethers (Triton X). Mixtures of surfactant molecules, including mixtures of surfactants of different chemical types, are acceptable. Surfactants should be suitable for pharmaceutical administration and compatible with the peptide to be delivered.

In certain embodiments, the emulsion may be limited in or substantially free of one or more cosurfactants selected from the group consisting of free fatty acids, mono- or diglycerides (fatty acid mono- or diesters of glycerol), aliphatic C3–C6 monoalcohols (exclusive of e.g. chlorobutanol or other haloalkyl alcohol preservative), polyglycerol fatty acid esters, or lysophosphatidyl choline. In many embodiments, the particular limited cosurfactant from the above group may constitute less than 5%, usually less than 1%, often less than 0.1%, relative to the weight of hydrophobic core component. In some embodiments, one or more cosurfactants may be present.

5.4 Continuous Aqueous Phase

The aqueous component will be the continuous phase of the emulsion and may be water, saline or any other suitable aqueous solution which can yield an isotonic and pH controlled preparation.

In addition, the compositions of the invention may also comprise conventional additives such as preservatives, osmotic agents or pressure regulators and antioxidants. Typical preservatives include Thimerosal, chlorbutanol, and methyl, ethyl, propyl or butyl parabens. Typical osmotic pressure regulators include glycerol and mannitol, with glycerol being preferred. The preferred oil phase antioxidant is α-tocopherol or α-tocopherol succinate. The aqueous phase may also include an antioxidant of a polyamine carboxylic acid such as ethylene diamino tetraacetic acid, or a pharmaceutically acceptable salt thereof.

5.5 Antigens

Since the SME particles provide a hydrophilic-lipophilic microenvironment, either water-soluble or lipid-soluble immunogens can be incorporated in the SME vaccines of the present invention. Examples of peptide antigens are: hydrophilic natural or synthetic peptides and proteins derived from bacteria, viruses and parasites, such as the recombinant gp160 envelope protein of the HIV virus; natural or synthetic glycoproteins derived from parasites, bacteria or viruses such as the native surface glycoprotein of Leishmania strain or subunit vaccines containing part of the glycopeptides alone or covalently conjugated to lipopeptides like lauryl-cystein hydrophobic foot; protein toxoids such as the Staphylococcus enterotoxin B toxoid, either chemically or physically inactivated; non-toxic bacterial surface structures (fimbrial adhesions) of Escherichia coli strains such as the Shiga-like Toxin B Subunit (SLT-B) and AF-R1, a pilus adhesion which is a virulence factor for RDEC-1 E. coli strain; outer membrane proteins of Neisseria meningitidis; Hepatitis B surface antigen; native or synthetic malaria antigens derived from different portions of Plasmodium falciparum, etc.

Examples of lipophilic or hydrophobic immunogens are lipopolysaccharides (LPS), such as detoxified LPS obtained from E. coli (Sigma Chemical Co., St. Louis, USA); Lipid A, the terminal portion of LPS, such as the one isolated from Salmonella minnesota R595 from List Biological Laboratories (CA, USA).

In some embodiments, the emulsion particles will be free or substantially free of the above or other nonbioactive proteins, i.e. less than 5%, usually less than 1%, and frequently less than 0.1% (w/w) protein relative to other particle components.

5.5.1 Shigella Antigens

LPS preparation. LPS was extracted from single isolates of S. flexneri 2a or S. sonnei by hot phenol by established methods (29). Alkaline-detoxified LPS (LPSad) was prepared by mild alkaline treatment as previously described.

5.6 Bioadhesive SME Vaccine Adjuvants

Submicron emulsion vaccine adjuvants of the present invention optionally may contain a bioadhesive macromolecule or polymer in an amount sufficient to confer bioadhesive properties. The bioadhesive macromolecule enhances the delivery and attachment of antigens on or through the target mucous surface conferring mucosal immunity. The bioadhesive macromolecule may be selected from acidic non-naturally occurring polymers, preferably having at least one acidic group per four repeating or monomeric subunit moieties, such as polyacrylic acid and/or polymethacrylic acid (e.g., Carbopol, Carbomer), poly(methylvinyl ether/maleic anhydride) copolymer, and their mixtures and copolymers; acidic synthetically modified natural polymers, such as carboxymethylcellulose (CMC); neutral synthetically modified natural polymers, such as (hydroxypropyl) methylcellulose; basic amine-bearing polymers such as chitosan; acidic polymers obtainable from natural sources, such as alginic acid, hyaluronic acid, pectin, gum tragacanth, and karaya gum; and neutral non-naturally occurring polymers, such as polyvinylalcohol; or their mixtures.

The ionizable polymers may be present as free acids, bases, or salts, usually in a final concentration of 0.01–0.5% (w/v).

As used herein, a polymer of an indicated monomeric subunit contains at least 75%, preferably at least 90%, and up to 100% of the indicated type of monomer subunit; a copolymer of an indicated type of monomeric subunit contains at least 10%, preferably at least 25% of that monomeric subunit.

A preferred bioadhesive macromolecule is the family of acrylic acid polymers and copolymers (e.g. CARBOPOL™). These contain the general structure:

One preferred group of polymers of acrylic acid is commercially available under the tradename CARBOPOL. CARBOPOL 934 is available in a pharmaceutical grade.

Preferred bioadhesive or mucoadhesive macromolecules have a molecular weight of at least 50 kDa, preferably at least 300 kDA, and most preferably at least 1,000 kDa. Favored polymeric ionizable mucoadhesive macromolecules have not less than 2 mole percent acidic groups (e.g. COOH, $SO_3H$) or basic groups ($NH_2$, NRH, $NR_2$), relative to the number of monomeric units. More preferably, the acidic or basic groups constitute at least 5 mole percent, more preferably 25 or even 50, up to 100 mole % relative to the number of monomeric units of the macromolecule.

Preferred macromolecules also are soluble in water throughout their relevant concentration range (0.01–0.5% w/v).

5.7 Methods of Preparation

A further embodiment of the invention relates to methods for preparation of submicron emulsion vaccine adjuvants intrinsically and extrinsically as extensively detailed in the examples. In general, SME intrinsic formulations are prepared by emulsifying the antigen together with the SME components, while SME extrinsic formulations are prepared by adding externally the antigen to previously prepared plain SME.

5.8 Dehydrated SME Adjuvants

A further aspect of the invention provides dehydrated emulsions, made by dehydrating the submicron emulsion of the types described herein. Dehydrated submicron emulsions may be stored for prolonged periods with minimal degradation, then reconstituted with water shortly before use. Residual water content in the dehydrated emulsion is usually less than 5% (w/w), commonly less than 2%, and often less than 1%.

Dehydration may be performed by standard methods, such as drying under reduced pressure; when the emulsion is frozen prior to dehydration, this low pressure evaporation is known as lyophilization. Freezing may be performed conveniently in a dry ice-acetone or ethyl alcohol bath. The pressure reduction may be achieved conveniently with a mechanical vacuum pump, usually fitted with a liquid nitrogen cold trap to protect the pump from contamination. Pressures in the low millitorr range, e.g. 10–50 millitorr, are routinely achievable but higher or lower pressures are sufficient.

A cryoprotectant or anticoalescent compound may be added to the emulsion prior to dehydration to inhibit flocculation and coalescence upon rehydration. The cryoprotectant may be of any type known in the art, including sugars and polysaccharides such as sucrose or trehalose, and non-natural polymers such as polyvinylpyrrolidone. Cryoprotectants are usually present at less than 25%, commonly 10%, more commonly 5%, 4% (w/v) or less in the emulsion before lyophilization.

A preferred category of cryoprotectants is amino acids and oligopeptides. Preferred amino acids include valine, leucine, isoleucine, lysine, methionine, threonine, serine, arginine, alanine, glycine, histidine, proline, phenylalanine, taurine, and carnitine, although any of the other natural amino acids may also be present. Amino acids may be of either D or L configuration, or a mixture; the natural L form is preferred. Amino acids may be present as their salts or esters, and as mixtures of amino acids or as pure species.

A particularly preferred amino acid is glycine, which may be present either in pure form or as a component of a mixture, e.g., in an hydrolyzate of collagen or other glycine-rich protein.

Mixtures of oligopeptides, especially di- and tripeptides, are another preferred type of cryoprotectant.

These may be prepared conveniently as partial protein hydrolyzates or enzymatic digests.

The cryoprotective amino acids or oligopeptides are generally present in the emulsion at a concentration of about 0.25 to 25% (w/w), preferably about 0.5 to 12% (w/w), more preferably about 1 to 10% (w/w) and commonly 3–6% (w/w).

Cryoprotectants and methods of making lyophilized submicron emulsions are taught in more detail in copending application "Dry Compositions for Preparing Submicron Emulsions", PCT U.S. application Ser. No. 93/01415, which is herein incorporated by reference.

5.5.1 Shigella Antigen Proteosome Complex

Proteosomes are preparations of neisserial outer membrane protein vesicles that have previously been shown to enhance the parenteral immunogenicit of peptides and other antigens hydrophobivcally complexed to them. Moreover, large-scale vaccine trials with such meningoccal outer membrane protein preparations noncovalently complexed to meningococcal polysaccharides have demonstrated that such vaccines are safe for human use. In the present study, we evaluated an acellular approach to induce type-specific anti-Shigella immunity using purified Shigella LPS. In particular, we evaluated the mucosal immunogenicity and efficacy in animal models of S. flexneri 2a and S. sonnei LPS hydrophobically complexed to proteosomes (prot-LPS). These Shigella vaccine candidates were designed for oral or intranasal administration in order to achieve direct sensitization of targeted mucosal tissues and thereby stimulate mucosal Ig production and local immunity.

Proteosome preparation. Outer membrane proteins from group B serotype 2b Neisseria meningitidis were extracted with detergent as described previously.

EXAMPLES

This invention is illustrated by the following nonlimiting examples:

Example 1

Preparation of Intrinsic-gp160-SME Vaccine

Antigen description and background: The urgency and high priority for developing an effective vaccine against the human immunodeficiency virus (HIV) are fully recognized. The reasons for using subunits of the virus as the basis of an HIV vaccine are the perceived overwhelming requirements for safety. Despite the high efficacy of many live attenuated viral vaccines, the requirement for product safety, especially in the case of retroviruses, has favored the subunit approach to the extent that all of the current candidate preparations in clinical prophylactic trials are of this type, being mainly gp160, the envelope protein of HIV, or part thereof. Studies have shown that gp160 attaches the virus to the cell and also facilitates the fusion of the cell and virus during the early stages of infection.

The gp160 antigen used in this example was supplied by MicroGeneSys Inc. This gp160 recombinant protein in alum-adjuvanted vaccine formulation is currently under evaluation in human clinical trials.

Preparation of Oil Phase

The oil phase was composed of MCT oil (2.0 g Mygliol 812, Hulls, Germany), lecithin (0.4 g, Lipoid E-80, Germany), and DL-α-tocopherol succinate (8.0 mg, Merck, Germany). The lipids and oil were weighed in a 250-ml beaker and mixed at room temperature using a magnetic stirrer during 2–4 hrs until a homogenous and almost clear solution was obtained.

Preparation of Water Phase

Polysorbate 80 (1% w/v, Montanox 80, DF, Seppic, France), Glycerol (2.2% w/v, Merck, Germany), EDTA (0.1% w/v, Merck, Germany), and purified water (to 100% w/v) were dissolved at room temperature in a 250-ml beaker by gentle shaking using a magnetic stirrer plate until a clear homogenous solution was obtained (about 15–20 min). A total volume of 40 ml of water phase was prepared. A vial containing 2.1 ml of gp160 recombinant protein (MicroGeneSys, Inc., CT, USA) at a concentration of 0.25 mg/ml in saline was added to the water phase and the mixture was gently shaken for 5 min.

Mixing of Oil and Water Phase

The oil phase was heated to 40° C. and added to the beaker containing the 40 ml of water phase. The mixture was gently stirred for 10–15 min at room temperature.

Preparation of Oil-in-Water Coarse Emulsion

An oil-in-water emulsion containing the antigen was prepared using the medium-sized dispenser and homogenizing unit Polytron PT3000 (Kinematica, Switzerland) at 3,600 rpm for 30 sec. The resultant micronsize emulsion was cooled at room temperature.

Sizing of Emulsion to Submicron Range

The droplet size of the emulsion obtained after Polytron step was lowered to the submicron (nanosize) range by submitting the emulsion to high shear homogenization using the Gaulin Microlab 70 High Pressure Homogenizer (APV Gaulin, Germany) at 800 bar pressure. A total of 10 cycles were performed. The particle size distribution of the resultant formulation was determined using an N4MD Coulter Particle Size Analyzer (Coulter Electronics, England). The differential weight % mode of the instrument indicated the existence of homogeneous population of SME droplets with a mean particle size distribution of 43±35 nm. The estimated final gp160 concentration in the formulation was 56 µg/ml.

Example 2

Preparation of Intrinsic-SME Vaccine Containing gp160 Complexed to Proteosomes Proteosomes are meningococcal outer membrane protein preparations purified from *Neisseria meningitidis* by detergent extraction and ammonium sulphate precipitation. They naturally form 20–100 nm diameter hydrophobic membranous vesicles. Antigens are non-covalently complexed to proteosomes via hydrophobic interactions by mixing the antigen and proteosomes in the presence of detergent and then is removing the detergent over a prescribed period of time, permitting hydrophobic interactions to occur in the system.

Proteosomes have previously been shown to enhance the parenteral immunogenicity of peptides, gangliosides, lipopolysaccharides and proteins hydrophobically complexed to them (Lowell, G. H., L. F. Smith, R. C. Seid and W. D. Zollinger, J. Exp. Med. 167: 658–663, 1988). (Lowell, G. H., W. R. Ballou, L. F. Smith, R. A. Wirtz, W. D. Zollinger and W. T. Hockmeyer. Science 240: 800–802, 1988; Lowell, G. H. 1990. In: New Generation Vaccines. G. C. Woodrow and M. M. Levine (eds.), Marcel Dekker, Inc., New York, p. 141–160). and have been shown to be safe for human use in vaccine trials involving tens of thousands of humans in the development of anti-meningococcal vaccines (Zollinger, W. D. New and Improved Vaccines Against Meningococcal Disease. In: New Generation Vaccines, G. C. Woodrow and M. M. Levine (eds.), Marcel Dekker, Inc., New York, p. 325–348). Furthermore, proteosomes confer mucosal immunogenicity upon non-immunogenic antigens when administered orally or intranasally. Such intranasal or oral proteosome vaccines induce up to 100% protection against lethal pneumonia or keratoconjunctivitis in experimental murine models of shigellosis (Orr, N., G. Robin, D. Cohen, R. Arnon and G. Lowell. 1993. Immunogenicity and efficacy of oral or intranasal *Shigella flexneri* 2a and *Shigella sonnei* proteosome-lipopolysaccharide vaccines in animal models. Infect. Immun. 61: 2390–2395).

Oil and aqueous phases were prepared as described in Example 1. A vial containing 2.5 mg of gp160 non-covalently complexed to proteosomes and suspended in saline was added to the water phase (40 ml total volume) and the mixture was gently shaken for 5 min. The subsequent steps involved in the preparation of the SME, i.e. mixing of oil and water phases, homogenization and sizing to submicron range were carried out as described in Example 1. The particle size volume % distribution of the resultant formulation showed a mean droplet size of 38±41 nm. The estimated final gp160 concentration in the formulation was 46 µg/ml.

Example 3

Preparation of Extrinsic-gp160-SME Vaccine

Extrinsic formulations of gp160 in SME were performed by preparing plain SME as described in Example 1, but in the absence of the antigen and adding externally the aqueous solution containing the gp160 to the plain SME by gently shaking for 15 min at room temperature. A total volume of 2.3 ml of plain SME (average droplet size of 50±36 nm) were mixed with 2.1 ml solution of gp160 in saline containing 1.1 mg protein to give a final gp160 concentration of 0.25 mg/ml.

Example 4

Preparation of Extrinsic-SME Vaccine Containing gp160 Complexed to Proteosomes Extrinsic formulation of gp160 conjugated to proteosomes in SME were performed by preparing plain SME as described in Example 1, but in the absence of the antigen and adding externally an aqueous dispersion of the gp160-conjugated to proteosomes to the plain SME by gently shaking for 15 min at room temperature. A total volume of 5.4 ml of plain SME (average droplet size of 50±36 nm) were mixed with 7.0 ml saline containing 3.1 mg of gp160 complexed to proteosomes to give a final gp160 concentration of 0.25 mg/ml.

Example 5

Preparation of Intrinsic-SME Vaccine Containing Staphylococcus Enterotoxin B Toxoid-F Antigen description and background: Staphylococcal enterotoxin B (SEB) is a potent toxin that causes food borne illness among civilians and military personnel stationed around the world and is identified as a lethal offensive military threat that endangers both military and civilian populations through aerosolization.

SEB infection in civilian populations is related to staphylococcal food poisoning by SEB and related toxins: also contributes to death from staphylococcal sepsis following overwhelming staph infection. It also causes staph scalded skin syndrome in kids—i.e. morbidity and mortality from staphylococcal infections (P. Marrack and J. Kappler, Science, vol. 248, pp. 705–711,).

Due to the similarity to the human response both in sensitivity and clinical signs and the lack of an established model for lethality to SEB delivered via the respiratory route in lower animal species, non-human primates have been the primary animal model for development of vaccines to protect against respiratory challenge with SEB. Early work indicated that monkeys develop decreased sensitivity to repeated mucosal administration of the toxin. This suggested that protection to SEB exposure might be provided by toxoid immunization. Studies in rhesus monkeys and other animals indicated that oral immunization with formalinized toxoid was ineffective against parenteral challenge whereas parenteral immunization with formalinized SEB toxid induced serum antibodies that recognized native SEB (Bergdoll, M. S. Enterotoxins. pp. 559–598 In: Staphylococci and Staphylococcal Infections, eds. C. S. F. Easmon and C. Adlam, Academic Press, London, 1983). In the latter studies, however, several parenterally immunized monkeys that acquired anti-SEB antibodies had severe immediate-type hypersensitivity reactions when challenged with SEB toxin. These adverse reactions suggested that the formalinized SEB toxoid alone was not a candidate for parenteral vaccine development. Additionally, as the military threat would be by aerosolization, it was determined that studies on protection provided by serum IgG to respiratory challenge as well as protective effects provided by anti-SEB secretory IgA in the respiratory tract were required.

Recently, two identical lots of formalinized SEB toxoid were made at Walter Reed Army Institute of Research, Washington D.C. (WRAIR) following previously described specifications (Kaminski, R., S. Grate, E. Aboud-Pirak, C. Hooper, T. Levin, I. Weiss, S. Amselem, R. Arnon and G. Lowell, 1993). Comparison of induction of respiratory IgA and serum Ig by intranasal and parenteral proteosome vaccines formulated with staphylococcal enterotoxin B toxoids or ricin peptides. In Proceedings of 1993 Medical Defense Bioscience Review, Baltimore, Md.). This WRAIR formalinized toxoid preparation designated Tox-F was non-toxic in rabbits at 0.5 mg/kg, the dose at which SEB toxin is invariably lethal. Furthermore, it was non-toxic in the murine D-galactosamine model of SEB toxicity even at 500 ug per BALB/c mouse; 50 ug of SEB is 100% lethal in such mice. The physical characteristics of Tox-F were similar to that described by Eldridge (Eldridge, J. H., Staas, J. K., Meulbroek, J. A., Tice, T. T. and Gilley, R. M. Biodegradable and biocompatible poly(DL-lactide-co-glycolide) microspheres as an adjuvant for staphylococcal enterotoxin B toxoid which enhances the level of toxin-neutralizing antibodies. Infect. Immun. 59: 2978–2986, 1991) in that SDS-PAGE gel of Tox-F showed two distinct bands with estimated MW of 23,000 and 46,000. Biologically, Tox-F also had the characteristics previously reported by Eldridge et al, namely in a Mouse Spleen Lymphocyte Proliferative Assay in which concentrations of SEB toxin of 0.37–10.0 µg/ml were mitogenic, Tox-F was entirely non-mitogenic at all concentrations tested (0.04–100.0 µg/ml).

Preparation of SEB-Toxoid F

Formalinized SEB-Toxoid (Tox-F) was prepared according to the method of Warren, J. R., Spero, L. and Metzger, J. F. 1983. J. Immunol. 111: 885–892 and as per Eldridge, J. H. et al. 1991, Infect. Immun. 59: 2978–2986 by formalin treatment for 30 days at 37° C., pH 7.5.

Preparation of SME
Preparation of Oil Phase

Oil phase was composed of MCT oil (0.77 g, Mygliol 812, Hulls, Germany), lecithin (0.14 g, Lipoid E-80, Germany) and DL-α-tocopherol succinate (9.0 mg, Merck, Germany). The lipids and oil were weighed in a 250-ml beaker and mixed at room temperature using a magnetic stirrer during 2–4 hours until a homogenous and almost clear solution was obtained.

Preparation of Water Phase

Polysorbate 80 (0.5% w/v, Montanox 80, DF, Seppic, France), Glycerol (2.2% w/v, Merck, Germany), EDTA (0.1% w/v, Merck, Germany), and purified water (to 100% w/v) were dissolved at room temperature in a 250-ml beaker by gently shaking using a magnetic stirrer plate until a clear homogenous solution was obtained (about 15–20 min). A total volume of 45 ml of water phase was prepared. A vial containing 10 ml of SEB-Toxoid F in 6.3 ml buffer was added to the water phase and the mixture was gently shaken for 5 min.

Preparation of Oil-in-Water Coarse Emulsion

An oil-in-water emulsion containing the antigen was prepared by heating the oil phase to 40° C. and mixing it with the water phase with the aid of a 10 ml glass pipette until a homogenous and milky dispersion was obtained. The resultant micronsize emulsion was cooled at room temperature.

Sizing of Emulsion to Submicron Range

Figure 1:
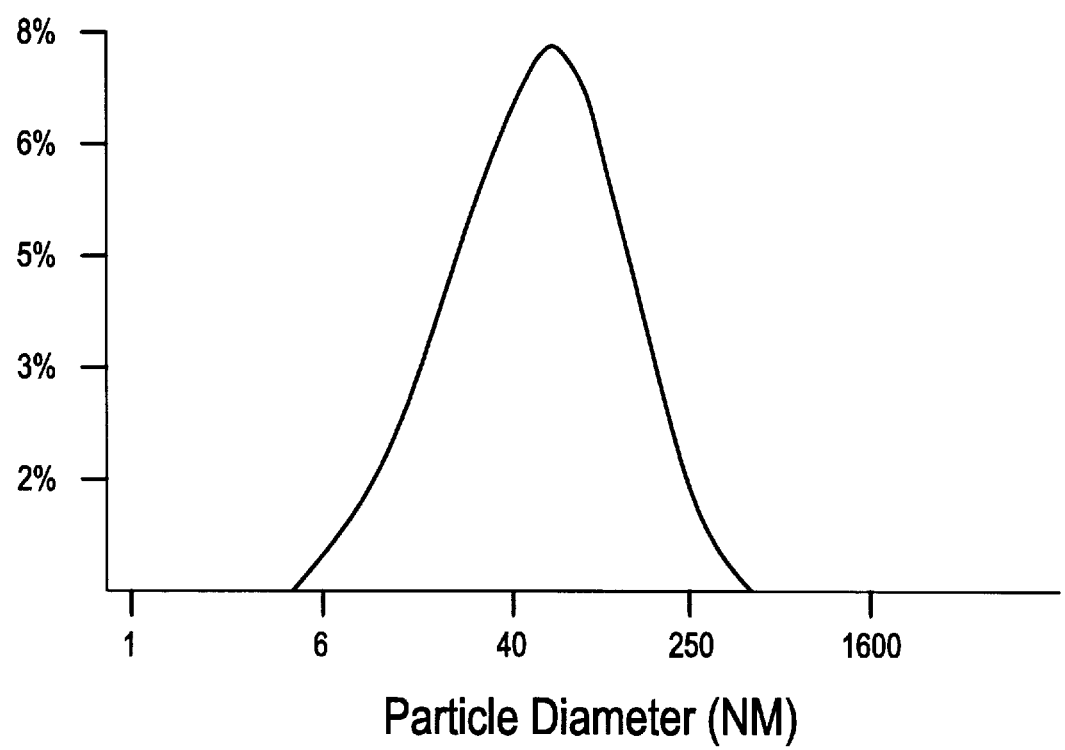
FIG. 1 is a graph showing the size distribution of Intrinsic-SME vaccine containing SEB-Toxoid F antigen.

The droplet size of the emulsion obtained after the Polytron step was lowered to submicron (nanosize) range by subjecting the emulsion to high shear homogenization using the Gaulin Microlab 70 High Pressure Homogenizer (APV Gaulin, Germany) at 800 bar pressure. A total of 5 cycles were performed. The particle size distribution of the resultant formulation was determined using an N4MD Coulter Particle Size Analyzer (Coulter Electronics, England). The differential weight % mode of the instrument indicated the existence of a single and homogenous population of SME droplets with a mean particle size distribution of 47.5±58 nm (see FIG. 1). The estimated final antigen concentration in the formulation was 220 µg/ml.

Example 6

Preparation of Entrinsic SME Vaccine Containing Staphylococcus Enterotoxin B Toxoid-F Extrinsic formulations of SEB-Toxoid-F in SME were performed by preparing plain SME as described in Example 5, but in the absence of the antigen and adding externally the aqueous solution containing the SEB-Toxoid-F to the plain SME by gently shaking for 15 min at room temperature. A total volume of 0.780 ml of stock SME were mixed with 0.780 ml solution of SEB-Toxoid-F in 0.01M Tris 0.15M NaCl buffer containing 0.780 mg protein to give a final SEB-Toxoid-F concentration of 0.500 mg/ml.

Example 7

Preparation of Entrinsic SME Vaccine Containing Staphylococcus Enterotoxin B Toxoid F Complexed to Proteosomes Extrinsic formulations of SEB-Toxoid-F in SME were performed by preparing plain SME as described in Example 5, but in the absence of the antigen and adding externally the aqueous solution containing the SEB-Toxoid-F complexed to proteosomes to the plain SME by gently shaking for 15 min at room temperature. A total volume of 0.780 ml of stock SME were mixed with 0.780 ml solution of SEB-Toxoid-F complexed to proteosomes in 0.01M Tris 0.15M NaCl buffer containing 0.780 mg protein to give a final SEB-Toxoid-F concentration of 0.500 mg/ml.

Example 8

Preparation of Extrinsic-SME Vaccine Containing Staphylococcus Enterotoxin B Toxoid C Preparation of SEB-Toxoid-C Carboxymethylated Toxoid (Tox-C): Carboxymethylated with 0.4 Bromoacetic Acid, pH 7.0 for 11 or 21 days in the dark at 20° C. as per Stema, G. N. and Bergdoll, M. S. 1982. Biophys. Biochem. Res. Commun. 105: 121–126 and as per Scheuber et al. 1985. Infect. Immunol. 50: 869–876. Made at WRAIR according to described methods.

Extrinsic formulations of SEB-Toxoid-C in SME were performed by preparing plain SME as described in Example 5, but in the absence of the antigen and adding externally the aqueous solution containing the SEB-Toxoid-C to the plain SME by gently shaking for 15 min at room temperature. A total volume of 0.165 ml of stock SME were mixed with 0.110 ml solution of SEB-Toxoid-C in water containing 0.110 mg protein to give a final SEB-Toxoid-C concentration of 0.400 mg/ml.

Example 9

Preparation of Entrinsic SME Vaccine Containing Staphylococcus Enterotoxin B Toxoid-C Complexed to Proteosomes Extrinsic formulations of SEB-Toxoid-C in SME were performed by preparing plain SME as described in Example 5, but in the absence of the antigen and adding externally the aqueous solution containing the SEB-Toxoid-C complexed to proteosomes to the plain SME by gentle shaking for 15 min at room temperature. A total volume of 0.045 ml of stock SME were mixed with 0.230 ml solution of SEB-Toxoid-C complexed to proteosomes in water containing 0.110 mg protein to give a final SEB-Toxoid-C concentration of 0.400 mg/ml.

Example 10

Preparation of Mucoadhesive Extrinsic SM Formulation Containing 0.05% Carbopol 420 ml of distilled water in which were dissolved 0.250 g Carbopol-940 (Goodrich, U.S.) and 11.2 g glycerol (isotonic agent), pH 3.82, were warmed to 45° C. and mixed with the oil phase, consisting of 21.2 g MCT oil (medium chain triglycerides, SIO, France), 3.74 g Lipoid E-75 (egg lecithin) and 1.5% w/v Emulfor EL-620 (Rhone-Poulenc, France), at a temperature of 60° C. After mixing by high speed stirrer (Polytron 3000, Kinematica, Switzerland) at 20,000 rpm for 5 minutes the mixture was dispersed by a high pressure homogenizer (Gaulin Microlab 70) at 700 bar for 5 minutes (approximately 10 cycles). The resulting emulsion was cooled, and after adjusting the pH to 5.0, the emulsion was filtered and packed in sterile bottles through a 0.2 $\mu$m filter.

After filtering, droplet size was measured by the photon correlation spectroscopy using a particle size analyzer (N4MD, Coulter Electronics, U.S.A.). The droplet size for carbopol containing droplets was 127±79 nm. This mucoadhesive composition was prepared as an extrinsic plain SME formulation to be added to the specific immunogen by gentle mixing.

Example 11

Figure 2A:
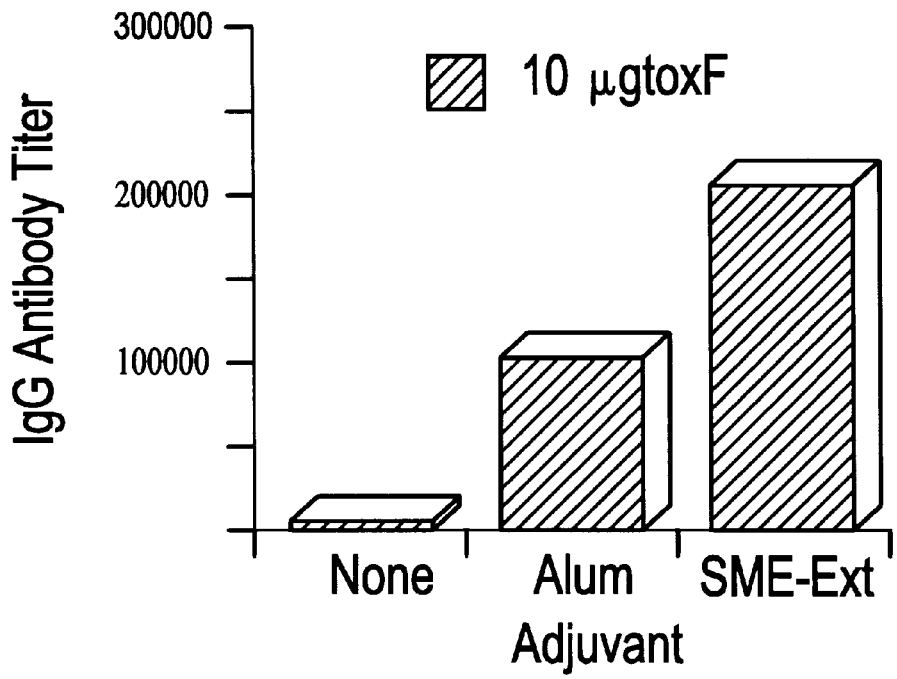
FIGS. 2A & 2B shows the immune response obtained after parenteral immunization with formalinized SEB-Toxoid (Toxoid F) at two different antigen doses 10 μg (A) and 50 μg (B) formulated in extrinsic-SME, intrinsic-SME, alum, or free antigen.
Figure 2B:
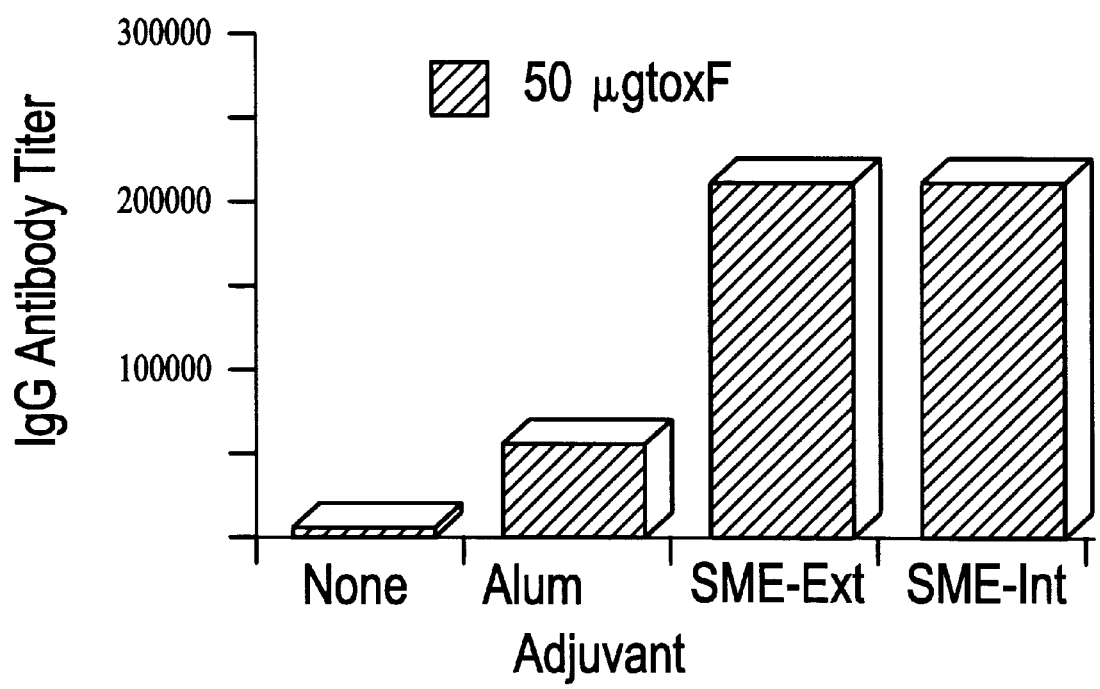
Figure 3:
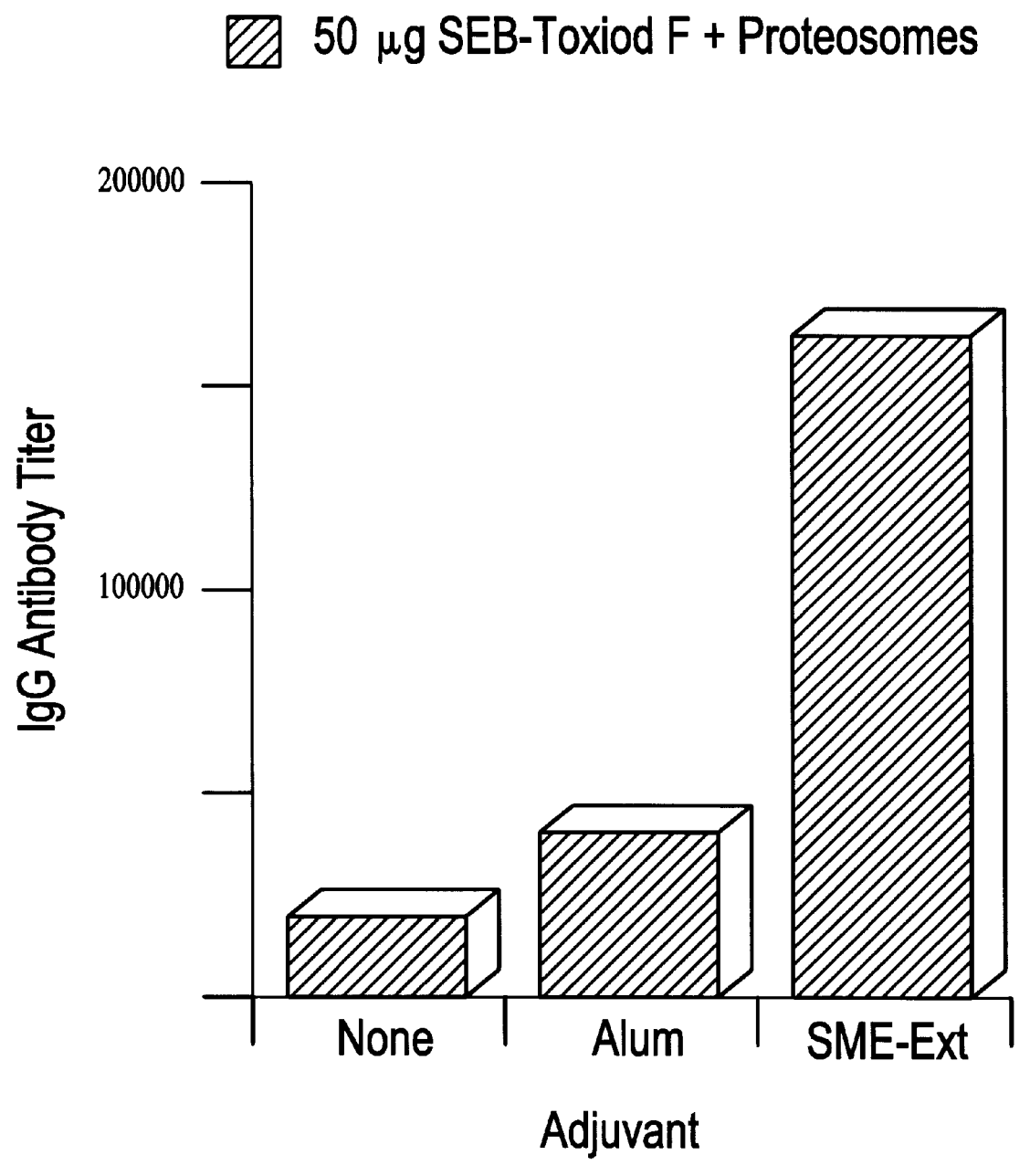

Enhanced Immunogencity to SEB Antigen after Parenteral Immunization with Intrinsic and Extrinsic SEB-Toxoid F-SME Vaccines Compared to Free Antigen or Alum-Adjuvanted Vaccine The antigen used was Staphylococcal Enterotoxin B (SEB) toxoid F alone or SEB toxoid complexed to meningococcal outer membrane proteosomes. This antigen was formulated with SME adjuvant either intrinsically or extrinsically, as described in Examples 5, 6 and 7, and compared to SEB toxoid-F alone or adjuvanted with alum. Outbred CD-1 mice, 5 animals/group, were immunized twice at approximately 3 week intervals by intramuscular injections with 10 or 50 $\mu$g doses of SEB Toxoid F. Sera, obtained after first and second immunizations, were analyzed by ELISA techniques using anti-SEB as the detecting antibody. As shown in FIGS. 2 and 3, intrinsic and extrinsic-SME formulations with (FIG. 2) or without proteosomes (FIG. 3) were effective in enhancing immunity to SEB antigens. In all the cases, the anti-SEB serum IgG titers obtained with the SME-adjuvant were several orders of magnitude higher than those obtained with the alum-adjuvanted formulation.

Example 12

Enhanced Immunogenicity to SEB Antigen after Parenteral Immunization with SEB-Toxoid-C SME Vaccines Compared to Free Antigen or Alum-Adjuvanted Vaccine.

The antigen used was carboxymethylated SEB-Toxoid or Toxoid-C. The antigen was incorporated extrinsically in SME, as described in Example 9. The immunization protocol and sera analysis for antibody activity was as described in Example 11. Mice were immunized intramuscularly with two 10 $\mu$g doses of Toxoid-C. As shown in Table 1, parenteral immunization with Toxoid-C-SME vaccine induced a 4-fold increase in the level of serum IgG even in the absence of proteosomes.

TABLE 1

Effects of formulation with saline, alum or submicron emulsion (SME) on parenteral (intramuscular) immunogenicity of carboxymethylated SEB toxoid (Toxoid-C)

| Antigen (2 doses) | Adjuvant | Anti-SEB serum IgG titer (OD > 0.5 at 1 hr) |
|---|---|---|
| SEB Toxoid-C | None (saline) | 819,200 |
| SEB Toxoid-C | Alum | 6,553,600 |
| SEB Toxoid-C | SME | 3,276,800 |

Example 13

Intranasal Immunization with SEB-Toxoid F SME Vaccines

Immunization against biologic threat agents, such as SEB requires the development of vaccines that can protect against respiratory challenge. The induction of respiratory IgA as well as serum Ig G is likely to be critically important to the success of such vaccines. To elicit effective respiratory, as well as systemic, immunity it may be necessary to develop a vaccine system that can be delivered intranasally, as well as parenterally.

BALB/c mice (8 animals/group) were immunized twice by intranasal slow dropwise instillation into both nostrils with SEB-Toxoid F (10 $\mu$g doses) formulated with or without proteosomes as a free antigen or adjuvanted with SME. Immunogenicity of these formulations was evaluated after the two immunizations by determining systemic IgG antibody activity against SEB and induction of anti-SEB respiratory IgA antibody titers.

As shown in Table 2, Toxoid-F formulated in extrinsic SME either with or without proteosomes conferred intranasal immunogenicity resulting in 500- to 2000-fold enhancement of anti-SEB serum IgG antibody activity.

TABLE 2

Effects of formulation of formalized SEB (Toxoid-F) with submicron emulsion (SME) and/or proteosomes on induction of anti-SEB serum IgG following intranasal immunization

| Antigen (2 doses) | Adjuvant | Anti-SEB serum IgG titers (O.D. > 0.5 at 1 hr) | |
|---|---|---|---|
| | | w/o protoeosomes | formulated with proteosomes |
| SEB Toxoid-F | None (saline) | 100 | 51,200 |
| SEB Toxoid-F | SME | 51,200 | 204,800 |

Extrinsic SME formation of Toxoid-F complexed to proteosomes also enhanced lung IgA antibody levels to SEB (Table 3).

TABLE 3

Enhanced production of anti-seb respiratory (lung) IgA antibodies after intranasal immunization of BALB/c mice with 10 μg SEB-Toxoid F antigen alone or adjuvanted with SME

| Antigen | Adjuvant | Anti-SEB lung IgA titer |
| --- | --- | --- |
| SEBtox-F | None (saline) | 0 |
| SEBtox-F | Extrinsic SME | 0 |
| SEBtox-F | Intrinsic SME | 0 |
| SEBtox-F-proteosomes | None (saline) | 0.6 |
| SEBtox-F-proteosomes | Extrinsic SME | 10 |

Example 14

Intranasal Immunization with Lipopolysaccharide (LPS) Antigen from S. flex complexed to proteosomes adjuvanted with Extrinsic-SME.

Evidence that the SME has potential as a mucosal adjuvant is also shown by the ability of the extrinsic-SME adjuvant formulation to markedly enhance the lung IgA of the proteosome-LPS antigen when given intranasally (Table 4) compared to the free antigen. The immunization protocol included two groups of BALB/c mice (4 animals each) which were immunized intranasally with 10 μg dose of LPS from S. flex complexed to proteosomes. The non-covalent complexation of LPS to proteosomes was carried out in a similar way as described in Example 2.

TABLE 4

Induction of mucosal immunity after intranasal immunization of Balb/C mice with 10 μg LPS-complexed to proteosomes as a free antigen or adjuvanted with extrinsic-SME

| Antigen | Adjuvant | Anti-S. flex Lung LPS IgA | | | |
| --- | --- | --- | --- | --- | --- |
| LPS (S. flex)-Proteosomes | None | 256 | 512 | 1024 | 2 |
| LPS (S. flex)-Proteosomes | Extrinsic-SME | >2048 | >2048 | >2048 | >2048 |

Example 15

Oral (Intragastric) Immunization of Mice with Lipopolysaccharide (LPS) Antigen from S. flex complexed to proteosomes adjuvanted with extrinsic-SME.

BALB/c mice (5 animals/group) were immunized orally (intragastrically) with 100 μg dose of LPS complexed to proteosomes and adjuvanted with extrinsic SME. As shown in Table 5, the SME adjuvant formulation was able to induce higher anti-S. flex LPS intestinal IgA titers, compared to the free antigen.

TABLE 5

Induction of mucosal immunity after oral (intragastric) immunization of Balb/C mice with LPS-complexed to proteosomes as a free antigen or adjuvanted with extrinsic-SME

| Antigen | Adjuvant | Anti S. flex LPS intestinal IgA |
| --- | --- | --- |
| LPS (S. flex)-proteosomes | None | 74 |
| LPS (S. flex)-proteosomes | Extrinsic-SME | 169 |

Example 16

Protection Against Systemic Challenge with SEB by SEB Toxoid Vaccines Formulated with SME Adjuvant Administered Parenterally or Intranasally Mice immunized parenterally (Table 6) or intranasally (Table 7) with Staphylococcus Enterotoxin B in mice immunized with SEB Toxoid-F vaccines formulated with SME or proteosomes were significantly protected against systemic SEB challenge (100 μg toxin).

TABLE 6

Correlation of anti-SEB serum IgG titers obtained after parenteral (i.m.) immunization (50 μg SEB-Toxoid F) with protection against systemic challenge with 100 μg SEB in CD-1 mice

| Antigen | Adjuvant | Anti-SEB IgG | died/total | Survival |
| --- | --- | --- | --- | --- |
| control | none | 0 | 10/18 | 44% |
| SEB-tox F | none | 3,200 | 3/5 | 40% |
| SEB-tox F | alum | 51,200 | 4/5 | 20% |
| SEB-tox F | SME-Extrinsic | 204,800 | 0/5 | 100% |
| SEB-tox F | SME-Intrinsic | 204,800 | 0/4 | 100% |

TABLE 7

Correlation of anti-SEB serum IgG titers with protection against systemic (im) challenge with 100 μg SEB in D-galactosamine-sensitized inbred (Balb/C) mice: effect of proteosomes and SME on efficacy of intranasal immunization with formalinized (Toxoid-F) SEB vaccines

| Vaccine | Adjuvant | Anti-SEB IgG serum titer | SEB challenge results #died/#total | Survived |
| --- | --- | --- | --- | --- |
| None | None | <50 | 12/12 | 0% |
| Toxoid-F | SME | 51,200 | 4/7 | 40% |
| Toxoid-F-Proteosomes | None | 409,600 | 2/5 | 60% |

The data in Table 6 show a very good correlation between the anti-SEB serum IgG titers obtained after intramuscular immunization of CD-1 mice with protection against systemic challenge with 100 μg of SEB. In the groups immunized with either extrinsic or intrinsic SME-SEB Toxoid F vaccines, the survival was 100% while for animals immunized with free antigen or alum-adjuvanted vaccine the survival was 0 and 40%, respectively.

Table 7 shows similar data for BALB/c mice immunized intranasally with SEB-Toxoid F alone or complexed to proteosomes in SME adjuvant or as free antigen.

Example 17

Enhanced Murine Immunogenicity of gp160 HIV Antigen Incorporated in SME Adjuvants Either Intrinsically or Extrinsically.

The antigens used were gp160 alone or gp160 complexed to meningococcal outer membrane proteosomes. These antigens were formulated with SME either intrinsically or extrinsically and compared to the gp160 used without an adjuvant, as described in Examples 1–4. Mice (5 animals/group) were immunized three times at 3–4 week intervals. Sera, obtained after 2 and 3 immunizations were analyzed for specific anti-gp160 peptide IgG responses by quantitative Western blot techniques using seven specific HIV epitopes as the detecting antigens. As shown in Table 8a, both intrinsic and extrinsic formulations of SME were effective in enhancing immunity to several gp160 epitopes. Note that the strongest and broadest anti-HIV responses were obtained with the intrinsic formulation using gp160-proteosomes as the antigen (rows 5 and 11 in Table 8a).

Example 18

Enhanced Lapine Immunogenicity of gp160 HIV Antigen Free or Complexed to Proteosomes Formulated in SME Vaccine Adjuvants.

The antigens used were gp160 alone or gp160 complexed to meningococcal outer membrane proteosomes. These antigens were formulated with SME either intrinsically or extrinsically and compared to gp160-alum, gp160-proteosomes, and gp160-proteosomes-alum formulations. Rabbits (4 animals/group) were immunized parenterally four times at different intervals. Sera, obtained after second, third and fourth immunizations were analyzed by for specific anti-gp160 peptide IgG responses by quantitative Western blot techniques using seven specific HIV epitopes as the detecting antigens. As shown in Table 8b, intrinsic formulations with SME with or without proteosomes were effective in enhancing immunity to several gp160 epitopes and even gp160 formulated with only an SEM-intrinsic preparation was as good as or better than gp160 formulated with alum, a known adjuvant currently used in people.

Figure 4:
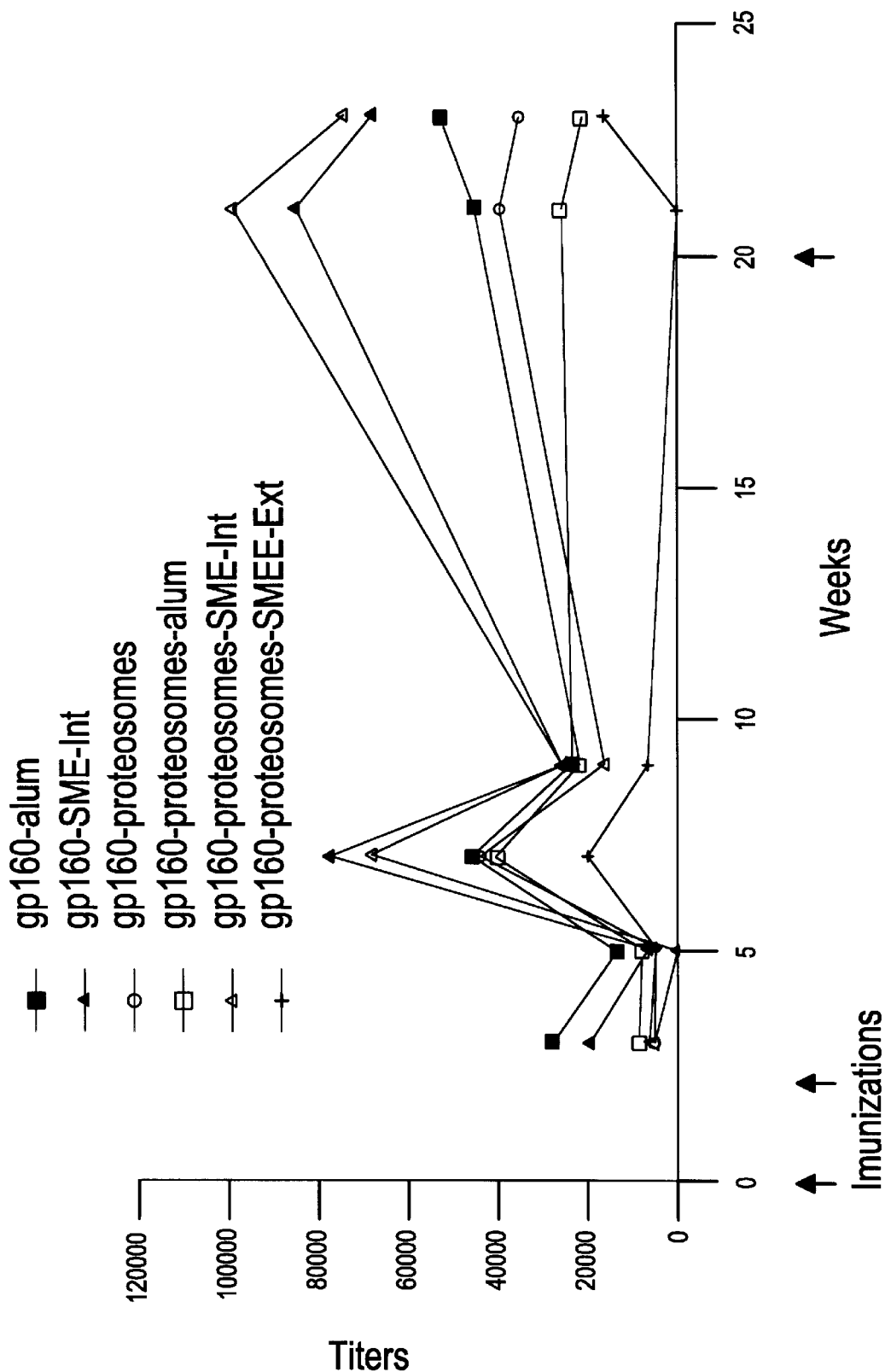
FIG. 4 shows the anti gp160 antibody rabbit titers obtained after parenteral immunization with gp160 formulated in alum, proteosomes or SME adjuvants.

Another analysis of the experiment showing adjuvant effects of SME with gp160 vaccines in rabbits in which the antigens used were gp160 alone or gp160 complexed to meningococcal outer membrane proteosomes is shown in FIG. 4. These antigens were formulated with SME either intrinsically or extrinsically and compared to gp160-alum, gp160-proteosomes, and gp160-proteosomes-alum formulations. Rabbits (4 animals per group) were immunized parenterally four times at different intervals. Sera, obtained after second, third and fourth immunizations were analyzed by ELISA techniques using several specific HIV epitopes as the detecting antigens. As shown in FIG. 4, intrinsic formulations with SME with or without proteosomes were effective in enhancing immunity to several gp160 epitopes.

Among the six groups tested, the intrinsic-SME vaccine formulation containing the gp160 antigen in the absence of alum, was the most effective vaccine eliciting the high antibody titers with improved and extended immunogenicity against several selected gp160 epitopes compared to the standard alum-adjuvanted vaccine actually in clinical trials.

Figure 5:
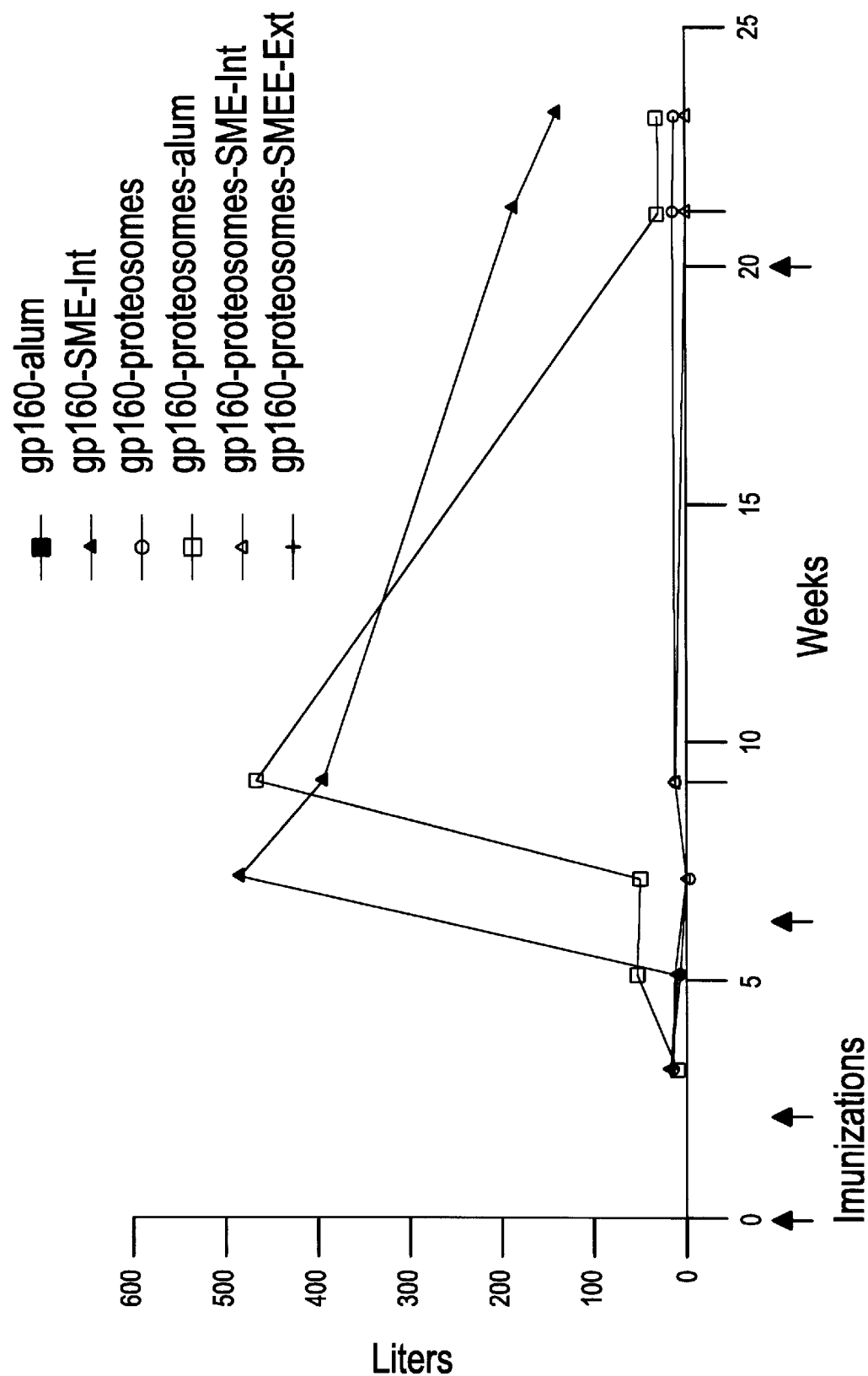
FIG. 5 shows the specific anti-Alex 10 (V3 loop) rabbit IgG titers obtained after parenteral immunization with gp160 formulated in alum, proteosomes or SME adjuvants.

More importantly, the SME-intrinsic formulation of gp160 was able to induce IgG antibodies against the V3 loop epitope of the gp160 molecule (FIG. 5), the site of the principal neutralizing determinant which blocks binding to CD4 (the main cellular receptor for HIV). Since the standard alum-adjuvanted formulation did not generate antibodies against the V3 peptide domain, the additional epitope recognition and enhanced total immunogenicity of SME-intrinsic adjuvant is considered to be a very significant achievement.

These data are encouraging for the development of enhanced subunit formulations of gp160 vaccines for HIV vaccine therapy.

Example 19

Immunogenicity of Leishmania Glycoproteins Formulated in Extrinsic-SME Adjuvant Either with or without Proteosomes

The gene for a surface protein antigen of *Leishmania major* gp63, has been cloned and sequenced. This protein, recombinantly expressed in live Salmonella, or given in a sub-unit vaccine as either the purified native gp63 or selected gp63 peptides (Jardim A., Alexander J., Teh S., Ou D, Olafson R. W. 1990. J. Exp. Med. 172: 645), has recently been shown to limit the extent of lesion development in murine models of cutaneous leishmaniasis when given with certain adjuvants. These results suggest that a vaccine to protect humans against leishmaniasis composed of defined purified components is a realistic goal. The sub-unit vaccines were effective, however, only when administered with adjuvants containing *Corynebacterium parvum* (CPV) and poloxamer 407. Other adjuvants (Complete Freund's Adjuvant, CFA), or lack of adjuvant exacerbated disease.

Major success was achieved with the discovery that subcutaneous immunization with one small gp63 peptide covalently conjugated to lauryl-cysteine protected against severe Leishmania cutaneous lesions with reduction of lesions in three separate experiments.

The objective in the present example was to demonstrate immunogenicity and efficacy of an SME-adjuvanted lipopeptide vaccine to protect against severe morbidity of cutaneous leishmaniasis in murine models.

TABLE 9

Effect of immunization with LC-467 Leishmania lipopeptide formulated in SME adjuvant either with or without proteosomes on lesion size

| Formulation | % decrease on lesion size from control in CBA mice |
| --- | --- |
| LC-467-proteosomes | 52 |
| LC-467-Extrinsic SME | 90 |
| LC-467-proteosomes-Extrinsic SME | 90 |

The antigens used were lipopeptides obtained from the major glycoprotein of the Leishmania parasite. The peptides (denoted 457 and 154) were covalently attached to lauryl cysteine to serve as the hydrophobic foot. The vaccine was prepared by gentle mixing of the antigens at room temperature with plain extrinsic-SME for 15 min.

Two animal models were used: (1) CBA mouse, model similar to human cutaneous disease; and (2) BALB/c mice, model similar to visceral Leishmania which is lethal if not treated.

The immunization protocol included two injections of the animals (8 mice/group) at weeks 0 and 3 with the experimental vaccines (50 µg peptide/mouse). At week 6 the mice were infected with live Leishmania parasites and the lesion size as function of time was measured and compared. The results were expressed as % decrease from control (PBS injection). Different vaccine formulations containing SME with or without proteosomes were tested. Appropriate control formulations were used.

All the formulations tested containing the 154 glycopeptide had no effect on lesion size, even if this vaccine contained proteosomes, SME or their combination. However, when the LC-467-glycopeptide was used, up to 90% decrease in lesion size was obtained by incorporation of the lipopeptide in SME, even in the absence of proteosomes (Table 8).

Since there is considerable homology among Leishmania strains, this peptide may have wide application in ameliorating lesions caused by other forms of Leishmania.

Example 20

Vaccine Preparation:

LPS or LPSad from *Shigella flexneri* 2a or *S. sonnei* and group B serotype 2b *Neisseria meningitides* outer membrane proteins were mixed at 1:1 ratio (w/w) in 1% Empigen (2 mg/ml final concentration of LPS/LPSad and protein). The mixture was dialyzed in 1000 DALTON molecular weight cutoff (MWCO) dialyzis bags against PBS at 4° C. for 10 days with daily buffer exchanges versus PBS or Tris saline buffer or their equivalent. Since both the proteosomes and the LPS are of very high molecular weight, it is obviously likely that dialysis membrane with MWCO of far greater than 1000 daltons can reasonably be used and similarly, the length of the dialysis time would be considerably shortened. The vaccine preparations, prot-LPS or prot-LPSad were kept at 4° C. and diluted to the specific concentration with PBS just prior to vaccination.

Example 21

Methods Used in Analysis of Vaccine Complex

CL-4B column: Samples of vaccine preparation were eluted through CL-4B column (2.5×40 cm) and fractions were collected. The various fractions were assayed for protein by the Bradford method (Bradford, M. M.. 1970. *Anal. Biochem.* 72:248.) with BSA as standard. The LPS level in each fraction was calculated by competition ELISA as follows: 100 ul samples from each column fraction were incubated with 300 ul of specific-LPS-positive guinea-pig serum diluted 1:150 in filler for 1 hr, 37° C. Homologous LPS samples ranging from 100 $\mu$g/ml to 3.125 $\mu$g/ml were incubated as standards. The incubated serum and samples or standards were placed in LPS-precoated and blocked 96 wells plates for 2 hrs, 37° C. and the plates were developed as described under ELISA. The LPS level in each fraction was calculated with the standard curve obtained from the LPS standards.

Example 21

Methods used in Analysis of Vaccine Complex
Methods used in Analysis of Vaccine
Immunogenicity and Efficacy Immunization:

1) Mice: balb\c, age 7–10 weeks, 4–5 per group were immunized with the specific antigens either orally or intranasally. Orally (P.O.): 100 ul PBS, 0.2M NaHCo$_3$ containing 100 $\mu$g LPS/LPSad or 200 $\mu$g prot-LPS/LPSad complex. Intranasally (I.N.): 25 ul PBS containing 10 $\mu$g LPS/LPSad or 20 ug prot-LPS/LPSad complex. Mice were anaesthetized prior to intranasal immunization. Four vaccine preparation were used: LPS, LPSad, prot-LPS, prot-LPSad. A control group was vaccinated with PBS, 0.2M NaHCo$_3$ (P.O.) or PBS (I.N.). The vaccines were given in four different protocols: (a) one dose (b) two doses one week apart, (c) two doses three week apart, and (d) three doses one and three weeks apart.

2) Guinea pigs: DH guinea pigs age 2–3 month were immunized with prot-LPS administrated either orally or intranasally. Orally: 200 ul PBS, 0.2M NaHCo$_3$ containing 200 ug prot-LPS complex or intranasally: 50 ul PBS containing 40 ug prot-LPS complex. The animals were aneasthesized in both cases.

Antibody Sampling:

1) Mouse lung wash: 9–11 days after the last immunization mice were sacrificed by CO$_2$ suffocation and lungs exposed. A canula was inserted into the trachea and using three-way stopcock, lungs were washed with 2 ml PBS, 0.1% BSA and wash fluids were collected.

2) Mouse intestinal wash: Following the lung wash, the small intestine was removed and 2 ml PBS, 0.1% BSA, 50 mM EDTA and 0.1 mg/ml soybean trypsin inhibitor were passed through and collected. PMSF (1 mM final concentration) was added to the intestine wash after collection. Both lung and intestine washes were vortexed vigorously and centrifuged to remove cells and debris, the supernatents were collected and kept at -20° C. until assayed.

Serum Preparation:

Sera were prepared from blood collected from the killed mice and kept at -20° C. until assayed. Blood from guinea pigs was collected via cardiopuncture under anaesthetization, serum was separated and kept at -20° C. until assayed.

ELISA:

The antibody level in the various extracts e.g. serum, intestinal wash and lung wash was determined as described (2). Briefly, 96 wells flat bottom high binding plates (Costar, Cambridge, Mass., US) were precoated with the specific LPS, blocked with BSA/casein and washed three times. Serially double diluted samples in blocking solution were incubated in the plates and after the incubation period, the plates were washed three times and alkaline-phosphatase conjugated anti-guinea pig or anti-mouse IgG/IgA diluted 1:1000 (Sigma, St. Louis, Mo., US) was added. Plates were then washed three times, substrate was added and the absorbance at 405 nm was detected. The antibody titer is expressed as the maximal dilution which gave an O.D. equal or above the indicated value after specific processing period.

Challenge in Guinea Pigs (Sereny Test):

Based on the standard challenge assay for the pathogenesis of shigellosis (Sereny, B.. 1957. *Acta Microbiol. Acad. Sci. Hung.* 4:367; Hartman, B. A. et al 1991. *Infec. and Immunol.* 59:4075.), the conjunctival sac of one eye of the animal was inoculated with 30 $\mu$l suspension containing about 1×10$^8$ bacteria and the eye lids were lightly massaged. Two to three days after inoculation, the eyes were screened for the level of keratoconjunctivitis developed.

Results of Vaccine Analysis, Immunogenicity and Efficacy

Complex Efficiency.

Figure 6:
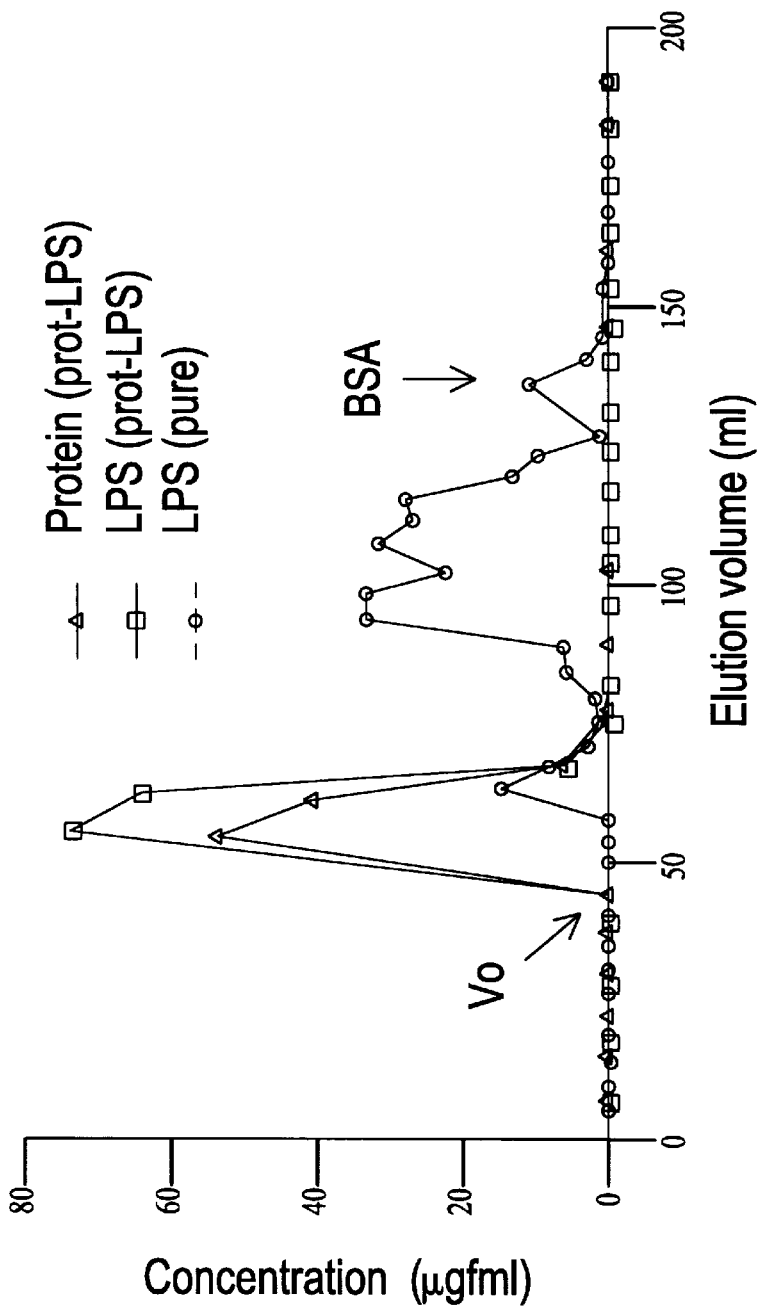
FIG. 6 is a graph depicting Protein (solid) and LPS (dashed) levels in fractions eluted from CL-4B column. (A) proteosome-LPS complex, (B) native *S. flexneri* 2a LPS.

FIG. 6 shows the protein and LPS patterns as measured after fractionation with CL-4B column. It is demonstrated that in the case of proteosome-LPS complex, the LPS and the proteosomes were detected at the same fractions at the void volume of the column (FIG. 1A). On the other hand, native LPS eluted much slower, thus, easily differentiated from complexed LPS (FIG. 1B).

Immunogenicity in Mice.

9–11 days after the last immunization, serum and secretions from intestines and lungs were collected and the specific antibody level was measured in ELISA. Proteosome-LPS complex has a remarkable advantage as compared to LPS, LPSad or prot-LPSad complex in inducing antibody production against *Shigella flexneri* 2a LPS in the serum (Table 10). Indeed, the inability of LPS alone, or even alkaline-detoxified LPS complexed to proteosomes (prot-LPSad) to give significant antibody levels emphasizes the remarkable specificity of the instant invention since only the native LPS complexed to proteosomes (Prot-LPS) was effective. Similar data were obtained with proteosomes complexed to LPS from *S. sonnei*. The LPS-specific antibody titer in serum of mice immunized with Proteosome-LPS complex after one, two or three doses of vaccine (FIG. 7) shows that the highest levels of IgA or IgG were achieved when the vaccine was given at 2 doses, 3 weeks apart or in 3 doses. In most cases, one dose of vaccine failed to elicit any detectable antibody levels in the serum as measured by ELISA after 1 hr incubation with the substrate. Longer incubation periods show induction of antibody production by the proteose-LPS complex even after one dose of vaccine (data not shown). There was no relative advantage to oral or intranasal routes in terms of serum antibody levels (FIG. 7). The specific anti-*S. flexneri* 2a LPS IgA levels in mice intestine shows a good correlation to the response observed in the serum in terms of the dose dependency and the lack of differences between oral and intranasal immunization (FIG. 8). Similar data was obtained using *S. sonnei* LPS complexed to proteosomes. In lungs however, intranasal immunization was more efficient in eliciting anti-*S. flexneri* 2a LPS IgA as compared to oral immunization (FIG. 8). Using *S. sonnei* LPS complexed to proteosomes, lung antibody levels were good using both routes.

TABLE 10

Anti-LPS IgG in mouse serum after two doses of vaccine 3 weeks apart

| | Anti-LPS IgG | | | |
|---|---|---|---|---|
| | Intranasal immunization | | Oral immunization | |
| Vaccine | GMT[a] | Range[b] | GMT[a] | Range[b] |
| *S. flexneri* 2a | | | | |
| LPS ad | <6 | | <6[c] | |
| Prot-LPSad | <6 | | 14[c] | 9–21 |
| LPS | <6 | | <6 | |
| Prot-LPS | 1,838 | 1,227–2,735 | 528 | 408–683 |
| *S. sonnei* | | | | |
| Prot-LPS | 4,222 | 3,200–5,571 | 113 | 27–467 |

[a]Geometric means of the maximal reciprocal dilution elicited an optical density greater than 0.5 after 1 h or incubation with substrate.
[b]GMT ± 1 standard error of mean.
[c]Three doses of vaccine at weeks 0, 1, and 4.

FIG. 9 depicts Table 10 of serum IgG levels in mice as determined by ELISA. Mice were immunized with two doses of vaccine at 0 and 3 weeks. Data are expressed as the maximal reciprocal dilution which gave at least the specified O.D.

Challenge in Guinea Pigs.

Following the results obtained with mice which emphasized the necessity of a booster dose, we vaccinated three groups of guinea pigs with prot-LPS preparation, all three groups were vaccinated either orally or intranasally. The first group was vaccinated with two doses of vaccine at 0 and 3 weeks and the second group was vaccinated with three doses at 0, 1 and 3 weeks. 12–14 days after the last vaccination, the guinea pigs were challenged (sereny test) with 30 μl PBS containing $7.6 \times 10^7$ (group 1), $10^8$ (group 2) or $2.6 \times 10^8$ (group 3) *S. flexneri* 2a (E22). Two or three days after the challenge, the animals were examined for keratoconjunctivitis. The animals could be sub-divided into three sub-groups upon the severity of infection observed. The results obtained in the sereny tests (Table 11) shows clearly that the prot-LPS complex was able to elicit in vivo protection against the homologous bacteria. The combined results shows that after intranasal immunization, 14 out of 19 animals were at least partially protected (p<0.001). After oral immunization, 11 out of 16 were at least partially protected (p<0.001) and 9 out of 16 were completely protected (p<0.001). All animals in the control groups (16 out of 16) were completely unprotected.

Similar experiments performed using *S. sonnei* LPS complexed to proteosomes showed that whereas 80% (e.g. 8 out of 10) guinea pigs were infected in control groups (Sereny test), 70% to 80% of guinea pigs immunized with two doses of *S. sonnei* LPS complexed to proteosomes were protected in three separate experiments. In these experiments, proteosomes from two different sources were used emphasizing the reproducibility of the vaccine. In addition, in the respiratory model of shigella infection developed by L. Hale et al, 90% (9 out of 10) swiss outbred mice challenged with shigella intranasally died whereas 75% (6 of 8) mice immunized orally twice with 100 ug of *S. sonnei* complexed to proteosomes survived thus confirming the efficacy of the vaccine even when challenged to induce death by respiratory infection.

Data from mice immunized with either the *S. flexneri* 2a or *S. sonnei* vaccines immunized either orally or intranasally also showed high levels of anti-meningococcal protein antibodies in sera, intestinal secretions and lung washes indicating the applicability of these vaccines to protect against meningococcal diseases as well.

TABLE 11

Homologous challenge (Sereny test) in guinea pigs after immunization with prot-*S. flexneri* 2a LPS

| | Route of immuniza-tion | No. infected with the following type of infection/total: | | | % Calculated protection | |
|---|---|---|---|---|---|---|
| Group | | None | Mild | Severe | Any Infection | Severe Infection |
| 1[a] | Intranasal | 0/6 | 1/6 | 5/6 | 0 | 17 |
| | Oral | 4/6 | 0/6 | 2/6 | 67 | 67 |
| | Control | 0/7 | 0/7 | 7/7 | | |
| 2[b] | Intranasal | 2/4 | 2/4 | 0/4 | 50 | 100 |
| | Oral | 4/4 | 0/4 | 0/4 | 100 | 100 |
| | Control | 0/4 | 0/4 | 4/4 | | |
| 3[c] | Intranasal | 2/9 | 7/9 | 0/9 | 22 | 100 |
| | Oral | 1/6 | 2/6 | 3/6 | 17 | 50 |
| | Control | 0/5 | 0/5 | 5/5 | | |
| 1 + 2 + 3 | Intranasal | 4/19 | 10/19 | 5/19 | 21 | 74 |
| | Oral | 9/16 | 2/16 | 5/16 | 56 | 69 |
| | Control | 0/16 | 0/16 | 16/16 | | |

[a]Immunization at 0 and 3 weeks; challenge with $7.6 \times 10^7$ bacteria per eye.
[b]Immunization at 0, 1, and 3 weeks; challenge with $1.0 \times 10^8$ bacteria per eye.
[c]Immunization at 0, 1, 3, and 8 weeks; challenge with $2.6 \times 10^8$ bacteria per eye.

Table 11 provides results of three challenge experiments in guinea pigs (Sereny test) wherein the animals were vaccinated with two doses at 0 and 3 weeks (group 1), three doses at 0, 1 and 3 weeks (group 2) or 4 doses.

6. INCORPORATION BY REFERENCE

To the extent necessary to understand or complete the disclosure of the present invention, all publications, patents, and patent applications mentioned herein are expressly incorporated by reference therein to the same extent as though each were individually so incorporated.

What is claimed is:

1. An immunogenic hydrophobic complex consisting essentially of proteosomes and at least one non-detoxified antigenic lipopolysaccharide.

2. The immunogenic hydrophobic complex of claim 1 wherein the lipopolysaccharide is isolated from Shigella.

3. The immunogenic hydrophobic complex of claim 2 wherein the Shigella is selected from the group consisting of S. flexneri 2a and Shigella sonnei or mixtures thereof.

4. The immunogenic hydrophobic complex of claim 1 wherein the proteosomes are derived from N. meningiditis.

5. The immunogenic hydrophobic complex of claim 1 wherein the proteosomes are derived from N. gonorrhea.

6. A vaccine comprising the immunogenic hydrophobic complex according to any one of claims 1, 2, 3, 4 and 5 and a carrier.

7. A method for providing enhanced immunogenicity comprising administering the vaccine of claim 6 to a subject parenterally, orally, intranasally or topically.

8. A method of achieving immunity by administering the vaccine of claim 6 to a subject parenterally, orally, intranasally or topically to impart immunity.

9. A method of achieving immunity according to claim 8 wherein the immunity is to gram negative bacterial infection.

10. A method of achieving immunity according to claim 9 wherein the immunity is to neisserial infection.

11. A method of achieving immunity according to claim 10 wherein the immunity is to gonococcal infection.

12. A method of achieving immunity according to claim 10 wherein the immunity is to meningococcal infection.

13. A method of achieving immunity according to claim 8 wherein the immunity is to shigellosis.

14. A method of achieving immunity according to claim 13 wherein the shigellosis immunity is to Shigella flexneri 2a.

15. A method of achieving immunity according to claim 13 wherein the shigellosis immunity is to Shigella sonnei.

16. A method of achieving immunity according to claim 8 by administering the vaccine to mucosal surfaces selected from the group of respiratory, gastrointestinal, vaginal, nasal, rectal and oral mucosa.

* * * * *